US006579833B1

(12) United States Patent
McNallan et al.

(10) Patent No.: US 6,579,833 B1
(45) Date of Patent: Jun. 17, 2003

(54) PROCESS FOR CONVERTING A METAL CARBIDE TO CARBON BY ETCHING IN HALOGENS

(75) Inventors: Michael J. McNallan, Oak Park, IL (US); Daniel Ersoy, Lincolnwood, IL (US); Yury Gogotsi, Lombard, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/568,312

(22) Filed: May 9, 2000

Related U.S. Application Data

(60) Provisional application No. 60/152,013, filed on Sep. 1, 1999.

(51) Int. Cl.[7] ....................... C10M 103/02; F16C 33/12
(52) U.S. Cl. ............................... 508/100; 508/109
(58) Field of Search ..................... 508/100, 109

(56) References Cited

U.S. PATENT DOCUMENTS

| | | | |
|---|---|---|---|
| 3,949,106 A | 4/1976 | Araki et al. | 427/249 |
| 3,977,896 A | 8/1976 | Bokros et al. | 427/213 |
| 4,016,304 A | 4/1977 | Beatty et al. | 427/6 |
| 4,173,522 A | 11/1979 | Pulker et al. | 204/192 C |
| 4,227,081 A | 10/1980 | Caputo et al. | 250/321 |
| 4,569,738 A | 2/1986 | Keiser et al. | 204/173 |
| 4,661,409 A | 4/1987 | Kieser et al. | 428/408 |
| 4,828,728 A * | 5/1989 | Dimigen et al. | |
| 5,298,286 A | 3/1994 | Yang et al. | 427/249 |
| 5,391,407 A | 2/1995 | Dearnaley | 427/527 |
| 5,393,572 A | 2/1995 | Dearnaley | 427/523 |
| 5,458,927 A | 10/1995 | Malaczynski et al. | 427/527 |
| 5,470,661 A | 11/1995 | Bailey et al. | 428/408 |
| 5,482,602 A | 1/1996 | Cooper et al. | 204/192.11 |
| 5,512,330 A | 4/1996 | Dearnaley | 427/525 |
| 5,725,573 A | 3/1998 | Dearnaley et al. | 623/2 |
| 5,731,045 A | 3/1998 | Dearnaley et al. | 427/527 |
| 5,731,046 A | 3/1998 | Mistry et al. | 427/553 |
| 6,051,751 A | 4/2000 | Shioshansi et al. | 623/16 |

FOREIGN PATENT DOCUMENTS

| | | |
|---|---|---|
| JP | 60067651 A | 4/1985 |
| JP | 63018077 A | 1/1988 |
| JP | 01246115 A | 10/1989 |
| JP | 02080300 A | 3/1990 |
| JP | 04238894 A | 8/1992 |
| JP | 05051205 A | 3/1993 |
| JP | 06024877 A | 2/1994 |
| JP | 10310494 A | 11/1998 |
| JP | 11268164 A | 10/1999 |
| JP | 11286778 A | 10/1999 |

OTHER PUBLICATIONS

Gogotsi, et al., "Formation Of Carbon Coatings On SiC Fibers By Selective Etching In Halogens And Supercritical Water", Ceram. Eng. Sci., vol. 19, No. 3, (1998), pp. 87–94 (Note: This issue of Ceramic Engineering and Science Proceedings contains the papers presented at the 22nd Annual Conference on Composites, Advanced Ceramics, Materials, and Structures, held at Cocoa Beach, Florida in Jan., 1998).

(List continued on next page.)

Primary Examiner—Jerry D. Johnson
(74) Attorney, Agent, or Firm—Marshall, Gerstein & Borun

(57) ABSTRACT

A process for the synthesis of carbon coatings on the surface of metal carbides, preferably SiC, by etching in a halogen-containing gaseous etchant, and optionally hydrogen gas, leading to (he formation of a carbon layer on the metal carbide. The reaction is performed in gas mixtures containing about 0% (trace) amounts to 100% halogen-containing gaseous etchant, e.g., $Cl_2$, and about 0% to 99.9% $H_2$ (hydrogen gas) at temperatures from about 100° C. to about 4,000° C., preferably about 800° C. to about 1,200° C., over any time range, maintaining a pressure of preferably about one atmosphere, to about 100 atmospheres.

8 Claims, 29 Drawing Sheets

OTHER PUBLICATIONS

Gogotsi, et al., "Carbon Coatings On Silicon Carbide By Reaction With Chlorine–Containing Gases", *Journal of Materials Chemistry*, vol. 7 (1997), pp. 1841–1848.

McNallan, et al., "Preparation Of Carbon Films By High Temperature Chlorination Of Metal Carbides", *Proceedings, Ninth International Conference on High Temperature Materials Chemistry*, PV 97–39, K.E. Spear, Ed., The Electrochemical Society, Inc., Pennington, NJ, 1997, pp. 529–536.

Jeon, et al., "Formation Of Carbon Coatings On Silicon Carbide By Reactions In Halogen Containing Media", *Fundamental Aspects of High Temperature Corrosion–VI*, PV 96–26, D.A. Shores, R.A. Rapp, P.Y. Hou, Eds., The Electrochemical Society, Inc., Pennington, NJ, 1996, pp. 256–268.

McNallan, et al., "Formation of Carbon Films on Ceramic Carbides by High Temperature Chlorination", *Tribology Issues and Opportunities in MEMS*, B. Bhushan, Ed., Kluwer Academic Publishers, Dordrecht, The Netherlands, 1998, pp. 559–565.

Jacob, et al., "Bulk Synthesis of Nanotube–Like Carbon Material", was distributed as a handout at the Annual Meeting of the Materials Research Society, in Boston, MA, Nov. 30, 1999.

"Skeleton C Breakthrough In The Synthesis Of Structured Elemental Carbon", was distributed as a handout at the Annual Meeting of the Materials Research Society in Boston, MA, Nov. 1999.

Ersoy, et al., "High Temperature Chlorination Of SIC For Preparation Of Tribological Carbon Films", (Electrochemical Society Proceedings vol. 98–9) proceedings of the symposium on high temperature corrosion and materials chemistry, San Diego, CA, USA, May 3–8, 1998, pp. 324–333.

* cited by examiner

| Hardness | 10 | 20 | 30 | 40 | 50 | 60 | 70 | 80 | 90 | 100 |
|---|---|---|---|---|---|---|---|---|---|---|
| Hardness | 11.6 | 25.9 | 9.5 | 1.7 | 0.6 | 0.6 | 0.5 | 1.0 | 0.6 | 0.7 |
| Displacement (nm)/10 | 19.1 | 13.9 | 22.2 | 57.2 | 99.0 | 98.4 | 105.7 | 81.0 | 99.6 | 95.2 |

PROCESS FOR CONVERTING A METAL CARBIDE TO CARBON BY ETCHING IN HALOGENS

CROSS-REFERENCE TO RELATED APPLICATION

This application claims priority from provisional application No. 60/152,013 filed Sep. 1, 1999.

This invention was made with government support under Grant CMS-9813400 awarded from the NSF Tribology and Surface Engineering Program.

FIELD OF THE INVENTION

This invention relates to a process for converting a metal carbide to carbon on a surface of a monolithic part that is predominantly a metal carbide or has predominantly a metal carbide surface, e.g., coating, by etching in a halogen-containing gas and more particularly, the uses of such materials having a converted carbon surface layer in environments that require long wear and low friction.

BACKGROUND OF THE INVENTION AND PRIOR ART

The extraction of silicon from silicon carbide powders and fibers by halogens ($F_2$, $Cl_2$, $Br_2$, $I_2$ or mixtures) or compounds containing one or more halogens (e.g., HF, $CCl_4$, and the like) can lead to the formation of free carbon—see Gogotsi, et al. "Carbon coatings on silicon carbide by reaction with chlorine-containing gases", J. Mater. Chem., pp. 1841–1848 (1997); and Gogotsi, et al. "Formation Of Carbon Coatings On SIC Fibers By Selective Etching In Halogens And Supercritical Water", 22nd Annual Conference on Composites, Advanced Ceramics, Materials, and Structures: A, *Ceramic Engineering and Science Proceedings*, Vol. 19, December 1998. This method can be used to obtain carbon from SiC, TiC, WC and other carbides to form volatile halides ($SiCl_4$ and $TiCl_4$ are typical examples), but do not form soluble oxides. This process can be considered as a reaction of the following type:

$$MC(s)+D(g)=C(s)+M_yD_x(g)+D_z(g),$$

where MC is a metal carbide, D is a gaseous halogen or halogen-containing etchant (e.g., $Cl_2$, HCl, and the like), $M_yD_x$ is a gaseous fragment reaction product species, and $D_z$ is another possible fragment reaction product species. This type of reaction can lead to the formation of free carbon, that may maintain the $sp^3$ structure which it has in carbide and form diamond. Alternatively, it can be transformed to graphite, or form various amorphous or disordered carbon structures intermediate to diamond and graphite.

Specifically, for the preferred metal carbide, silicon carbide, the chlorination reactions:

$$SiC(s)+2Cl_2(g)=SiCl_4(g)+C(s) \text{ and}$$

$$SiC(s)+4HCl(g)=SiCl_4(g)+C(s)+2H_2(g)$$

lead to the formation of a carbon surface, or a carbon coating, on the surface of metal carbides or to the complete transformation of carbide particles into carbon. This is due to the fact that a metal-halogen, e.g., $SiCl_4$, is much more thermodynamically stable than a carbon-halogen, e.g., $CCl_4$, at elevated temperatures, so that chlorine reacts selectively with the Si at SiC surfaces leaving carbon behind. The structure of the carbon layer is affected by temperature and by the composition of the chlorinating gas mixture. In accordance with the present invention carbon films or surface layers were formed as an integral part of monolithic metal carbide parts on the surface of commercially available monolithic α-SiC and β-SiC specimens by high temperature (100° C. or greater) chlorination at atmospheric pressure in $H_2$—$Cl_2$ and $Cl_2$ gas mixtures, using an inert gas, such as Argon, to dilute the halogen gas content to a desired concentration.

Commercial methods of synthesis of carbon coatings have serious limitations. The CVD method does not allow the synthesis of coatings on powders and other particulate materials. Heteroepitaxial growth of diamond by CVD still has its problems. Generally CVD and Physical Vapor Deposition (PVD) processes exhibit low rates of deposition and require a nucleation pre-treatment for diamond synthesis—see Yang, U.S. Pat. No. 5,298,286—March 1994. Plasma-assisted CVD is especially slow and energy-consuming technique—see Kieser, U.S. Pat. No. 4,661,409—April 1987, and U.S. Pat. No. 4,569,738—February 1986. Moreover, carbon films deposited with the CVD and PVD methods do not generally adhere to the substrate, often peeling off during loading which can take place in tribological applications of carbon coatings, such as in cutting tools, bearings, seals, and the like. Special techniques used to improve adhesion between diamond films and other ceramic substrates have not been completely successful, particularly on WC tools because of the large differences in physical properties between diamond and WC. Other methods that have been used to produce carbon films with special properties include laser vaporization—see Mistry, U.S. Pat. No. 5,731,046—March 1998; high temperature synthesis, sputtering—Pulker, U.S. Pat. No. 4,173,522—November 1979; pyrolisis—Beatty, U.S. Pat. No. 4,016,304—April 1977, Bokros, U.S. Pat. No. 3,977,896—August 1976, Araki, U.S. Pat. No. 3,949,106—April 1976; decomposition of organic materials and ion beam deposition—Dearnaley, U.S. Pat. No. 5,731,045; 5,725,573—March 1998, U.S. Pat. No. 5,512,330—April 1996, U.S. Pat. No. 5,393,572—February 1995, U.S. Pat. No. 5,391,407—February 1995, Cooper U.S. Pat. No. 5,482,602—January 1996, Bailey, U.S. Pat. No. 5,470,661—November 1995, and Malaczynski, U.S. Pat. No. 5,458,927—October 1995. Most of these processes are expensive and energy-intensive. Additionally, there is no single versatile method that could provide all types of carbon coatings.

Another process which could be used to synthesize carbon coatings on the surface of carbides is by hydrothermal leaching—see Gogotsi, Ukrainian Patent 10393A; and Yoshimura, Japanese Patent 07,232,978. Both graphitic carbon and diamond can be obtained by interaction of SIC with water. However, the hydrothermal method can only be applied to carbides that form soluble or volatile hydroxides, such as $Si(OH)_4$. Additionally, the use of high-pressure autoclaves in hydrothermal synthesis can make scaling up of hydrothermal reactors difficult and expensive.

SUMMARY OF THE INVENTION

In brief by treating a metal carbide, preferably a monolithic part that is predominantly a metal carbide or has predominantly a metal carbide surface, e.g., coating, with a gaseous halogen, in accordance with the principles of the present invention, carbon coatings or surface layers are obtained that have an improved interfacial strength compared to prior art methods because the carbon is not deposited from the environment, rather the carbide surface is converted into carbon. This leads to an improved adhesion and decreased (or elimination of) delamination of the carbon coating.

Low cost: virtually any possible carbon structure (amorphous carbon, graphite, diamond, diamond like carbon, and the like) can be obtained on the surface of commercially available metal carbides by simply tuning the gas composition and/or temperature. This allows the use of the same reactor vessel, of almost any volume, for all types of carbon coatings.

The process of the present invention can be carried out at atmospheric pressure and does not require plasma or other high-energy sources.

Impure raw SiC can be used in accordance with the present invention containing predominantly (more than 50% by weight) SiC, preferably at least 80% SiC, because halogenation will remove most metallic impurities from the predominantly SiC material, thus improving the purity of SiC.

Unlike CVD, not only carbide components or fibers can be coated, but also powders, whiskers and platelets.

Monolithic parts with complex shapes and surface morphologies can be "coated" in accordance with the present invention. It is the reaction gas at atmospheric pressure in contact with the carbide surface that transforms the material. This is important for two reasons. First, the reaction can proceed anywhere the gas can reach, e.g., crevices, channels, intricate layered surfaces, holes, etc. This would be impossible with most of the other current available processes. Second, it allows control of growth on the atomic level.

Templating of the surface structure/coating will allow various ore sizes (angstroms to nanometers).

The process of the present invention is environmentally friendly technology since it can be operational as a closed loop process with the recovery of Si by decomposition of the metal halide, e.g., $SiCl_4$, and returning the halogen gas to the manufacturing process.

One object of the present invention is to provide a new method of producing carbon layers at low cost on metal carbides with virtually any possible carbon structure (amorphous carbon, graphite, diamond, diamond like carbon, etc.) can be obtained on the surface of commercially available SiC (and other metal carbides).

Another object of the invention is to provide improved interfacial strength between the carbon layer and the substrate metal carbide compared to other methods.

A further object of the invention is to provide a new method of carbon layer formation (coating) that allows the use of the same reactor vessel, of almost any volume, for all types of coatings desired.

Yet another object of the invention is to provide a new method of carbon coating on metal carbides at atmospheric pressure vs. higher pressures or lower pressures (vacuum) (which are most dangerous and expensive, and slow).

Still yet another object of the invention is to provide a new method of carbon coating on metal carbides that does not require plasma or other expensive high-energy sources.

Another object of the invention is to allow the use of impure, raw SiC (or other metal carbide) to be used (hence save money) in the production of coated metal carbides.

Another object of the invention is to allow not only carbide components or fibers to be coated, but also powders, whiskers and platelets (not possible with current processes, CVD, PVD, and the like).

A further object of the invention is to allow parts with complex shapes and surface morphologies to be coated, e.g., crevices, channels, intricate layered surfaces, holes, etc.

Yet another object of the invention is to allow control of carbon coating growth on the atomic level.

Still yet another object of the invention is to allow variation in pore sizes (angstroms to nanometers) of carbon coatings to tailor surface properties.

Another object of the invention is to provide a new environmentally friendly technology for coating of metal carbides.

The above and other objects and advantages of the present invention will become more apparent from the following detailed description of the preferred embodiments, read in conjunction with the drawings.

BRIEF DESCRIPTION OF THE DRAWINGS

FIG. 19 is a graph showing friction coefficient for treated (2% $Cl_2$, 0.75% $H_2$, 19 hours @1,000° C.) SiC vs. untreated SiC showing that the treated SiC has a relatively constant coefficient of friction of less than 0.15 vs. about 0.55 to $0.8^+$ for untreated;

FIG. 22 is a graph showing the coefficient of friction results of a pin-on-disk tribology test in both dry and wet environments showing that metal carbides treated in accordance with the present invention maintains its law coefficient of friction even when submersed under water;

Figure 1:
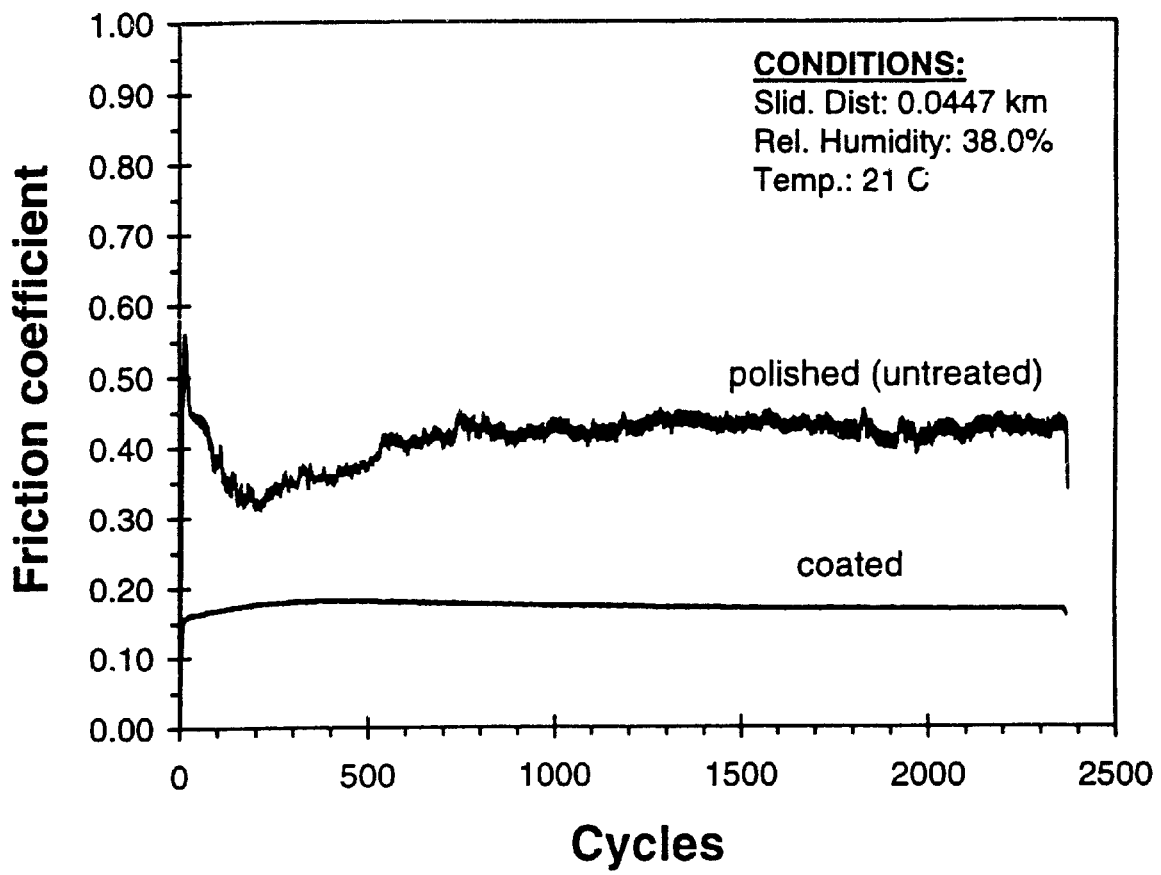
FIG. 1 is a graph comparing the friction coefficient of polished SiC (untreated) to SiC (treated) that has been halogen gas etched in 2.6% $Cl_2$, 1.3% $H_2$ and Ar for 24 hours at 1,000° C.

Other objects and advantages of the present invention will become apparent from the following detailed description of the preferred embodiments, taken in connection with the accompanying drawings, wherein, by way of illustration and example, an embodiment of the present invention is disclosed.

The present invention is directed to a process for the synthesis of carbon coatings on the surface of metal carbides by etching in halogens comprising the steps of the reaction of a metal carbide with a halogen gas, or a halogen-containing gaseous etchant and optionally hydrogen gas, leading to the formation of a gaseous fragment reaction product species and possibly other fragment species, leading to the formation of a carbon surface layer on the metal carbide. The reaction is performed in gas mixtures containing about 0% (trace) amounts to 100% gaseous halogen-containing etchant and about 0% to slightly less than 100% of $H_2$ (hydrogen gas), e.g., 0% to about 99.999%, at temperatures from about 100° C. to about 4,000° C. over any time range, maintaining a pressure of about 0.001 atmosphere, preferably about one atmosphere, to about 100 atmospheres, and leading to the formation of said carbon layer on the surface of the metal carbide or to the complete transformation of the carbide material into carbon of various structures.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriate detailed system, structure or manner.

The preferred metal carbide is silicon carbide, SiC, preferably α-SiC, however the process of the present invention can be performed on any metal carbide. The following two articles, hereby incorporated by reference, written by McNallan, Gogotsi, and Jeon, describe $Cl_2$ etching of TiC and TaC starting materials: Proceedings of the NFS/ASME Workshop on Tribology Issues and Opportunities in MEMS, Klumer Academic Publishers, pages 559–565 (1998); and Preparation of Carbon Films by High Temperature Chlorination of Metal Carbides, High Temperature Materials Chemistry, Electrochemical Society Proceedings Volume 97–39, pages 529–536 (1997); both articles hereby incorporated by reference. Examples of suitable metal carbides are shown in Table 1, as follows:

TABLE 1

Carbide Compounds

| Carbide | | CAS Registry Number | Formula |
|---|---|---|---|
| aluminum carbide | (4:3) | [1299-86-1] | $Al_4C_3$ |
| arsenic carbide | (2:6) | | $As_2C_6$ |
| beryllium carbide | (2:1) | [57788-94-0] | $Be_2C$ |
| boron carbide | (4:1) | [12069-32-8] | $B_4C$ |
| calcium carbide | (2:1) | [75-20-7] | $CaC_2$ |
| chromium carbide | (1:1) | [12011-60-8] | $CrC$ |
| chromium carbide | (3:2) | [12012-35-0] | $Cr_3C_2$ |
| chromium carbide | (4:1) | [12075-40-7] | $Cr_4C$ |
| chromium carbide | (7:3) | [12075-40-0] | $Cr_7C_3$ |
| chromium carbide | (23:6) | [12105-81-6] | $Cr_{23}C_6$ |
| cobalt carbide | (3:1) | [12011-59-5] | $Co_3C$ |
| cobalt tungsten carbide | (6:6:1) | [12538-07-7] | $Co_6W_6C$ |
| hafnium carbide | (1:1) | [12069-85-1] | $HfC$ |
| iron carbide | (1:1) | [12069-60-2] | $FeC$ |
| iron carbide | (2:1) | [12011-66-4] | $Fe_2C$ |
| iron carbide | (3:1) | [12011-67-5] | $Fe_3C$ |
| iron carbide | (3:1) | [12169-32-3] | $Fe_3C$ |
| iron carbide | (5:2) | [12127-45-6] | $Fe_5C_2$ |
| iron carbide | (7:3) | [12075-42-2] | $Fe_7C_3$ |
| iron carbide | (23:6) | [12012-72-5] | $Fe_{23}C_6$ |
| lanthanum carbide | (1:2) | [12071-15-7] | $LaC_2$ |
| manganese carbide | (3:1) | [12121-90-3] | $Mn_3C$ |
| manganese carbide | (23:6) | [12266-65-8] | $Mn_{23}C_6$ |
| magnesium carbide | (1:2) | [12122-46-2] | $MgC_2$ |
| magnesium carbide | (2:3) | [12151-74-5] | $Mg_2C_3$ |
| molybdenum carbide | (1:1) | [12011-97-1] | $MoC$ |
| molybdenum carbide | (2:1) | [12069-89-5] | $Mo_2C$ |
| molybdenum carbide | (23:6) | [12152-15-7] | $Mo_{23}C_6$ |
| nickel carbide | (1:1) | [12167-08-7] | $NiC$ |
| nickel carbide | (3:1) | [12012-02-1] | $Ni_3C$ |
| niobium carbide | (1:1) | [12069-94-2] | $NbC$ |
| niobium carbide | (2:1) | [12011-99-3] | $Nb_2C$ |
| plutonium carbide | (1:1) | [12070-03-0] | $PuC$ |
| plutonium carbide | (2:3) | [12076-56-1] | $Pu_2C_3$ |
| phosphorus carbide | (2:6) | | $P_2C_6$ |
| scandium carbide | (1:1) | [12012-14-5] | $ScC$ |
| silicon carbide | (1:1) | [409-21-2] | $SiC$ |
| tantalum carbide | (1:1) | [12070-06-3] | $TaC$ |
| tantalum carbide | (2:1) | [12070-07-4] | $Ta_2C$ |
| thorium carbide | (1:1) | [12012-16-6] | $ThC$ |
| thorium carbide | (1:2) | [12071-31-7] | $ThC_2$ |
| titanium carbide | (1:1) | [12070-08-5] | $TiC$ |
| tungsten carbide | (1:1) | [12070-12-1] | $EC$ |
| tungsten carbide | (2:1) | [12070-13-2] | $W_2C$ |
| uranium carbide | (1:1) | [12170-09-6] | $UC$ |
| uranium carbide | (1:2) | [12071-33-9] | $UC_2$ |
| uranium carbide | (2:3) | [12076-62-9] | $U_2C_3$ |
| vanadium carbide | (1:1) | [12070-10-9] | $VC$ |
| vanadium carbide | (2:1) | [12012-17-8] | $V_2C$ |
| zirconium carbide | (1:1) | [12020-14-3] | $ZrC$ |

The process of the present invention is inherently different from other coating processes in that the material (carbide surface) is actually transformed into a new material (carbon based) from the surface down into the material. This differs from "film" or coating applications which are applied or grown on top of the bulk material. In accordance with the present invention, carbon layers are formed on the surface of metal carbides by etching in halogens with or without the additional presence of hydrogen gas. This is accomplished by reacting the carbides with a reaction gas which contains from 0% (trace) to 100% halogen etchant and from 0% (trace) to 100% hydrogen gas in a reaction vessel at a temperature between 100° C. to 4,000° C. at a pressure between 0 atmospheres and 100 atmospheres, preferably about 1 atmosphere. In the preferred embodiment, the temperature is between 800 and 1,200° C. and at atmospheric pressure (about one atmosphere) with the metal carbide being silicon carbide and the halogen etchant being chlorine gas.

The advantages of this method are the adherence of the film or coating. The interface is where the coating "grows into" the bulk, providing excellent resistance to fracture and wear. In addition, since the method of the present invention does not add a coating material on top of the carbide, but rather transforms the metal carbide into carbon, one can achieve a complete transformation of carbide material into carbon of various structures. These structures can be, but are not limited to: diamond, diamond like carbon, ordered and disordered graphite, amorphous carbon, active carbon, and hydrogenated carbon. The $sp^2$ to $sp^3$ carbon bond type can be varied.

Highly disordered or amorphous carbon/graphite has a number of attractive applications, especially when combined as a coating on metal carbides, particularly silicon carbide. Acting as a solid lubricant on SiC, graphite's low friction coefficient can provide advantages in applications such as heavy-load bearings, brake pads, nanocoatings for microelectromechanical systems (MEMS), electrical connections, bio-implants, liquid and vapor dynamic seals, and the like.

Extraction of metals from carbides by chlorine leads to the formation of free carbon with various structures and carbon films can be produced on SiC surfaces by high temperature chlorination. Since $SiCl_4$ is much more thermodynamically stable than $CCl_4$ at elevated temperatures, chlorine reacts selectively with the silicon at SiC surfaces, leaving carbon behind, over the SiC substrate.

Ceramics show no or very limited plastic flow at room temperature and the adhesion force between two ceramics sliding is much lower than clean metal surfaces in contact. The value of friction coefficient, $\mu$, for ceramic-ceramic contacts lies typically in the range from 0.25 to 0.80. These are similar to values seen for metallic couples sliding in air in the presence of intact oxide films. Environmental factors are responsible for a wide variation in reported $\mu$ values. Despite their reputation for chemical inertness, most ceramics are susceptible to tribochemical reactions which form films and modify friction behavior. Also non-oxide ceramics, like SiC, have been found to react significantly with oxygen and/or water vapor to form oxide films on sliding surface. In the case of non-oxide ceramics, these oxides may then be hydrated which lowers the films shear strength and therefore the coefficient of friction.

The effects of surface films can be very marked: diamond shows high friction when sliding against itself in vacuum: $\mu$ reaches approximately 1. Yet in air, much lower friction is measured: $\mu$=0.05 to 0.15. The surface modification is most likely to be due to adsorption of gaseous species.

In graphite, the interplanar bonding is primarily from the van der Waals forces, with a weak covalent contribution resulting from interaction between the π-electron orbitals of the carbon atoms. The interplanar bond energy is about one tenth to one hundredth of that between atoms within the layers. The low friction of graphite is associated with its lamellar structure and this weak bonding. The sliding friction of graphite against itself or other materials in air is low; typically $\mu$=0.1. If the surface of the graphite is examined by electron diffraction after sliding, it is found that the basal planes have become oriented nearly parallel to the plane of the interface, with a misalignment of about five degrees.

The friction of graphite depends strongly on the nature of the ambient atmosphere. In vacuum or dry nitrogen, $\mu$ is typically ten times greater than in the ambient atmosphere. Controlled additions of air, water vapor, and the like reveal that the low friction and wear of graphite depends on the presence of oxygen, water vapor or other condensable vapors. The friction between graphite lamellae in their planes appears always to be low; they are low-energy surfaces and show little adhesion. However, the edges of the lamellae are high-energy sites, and bond strongly to other edge sites or to basal planes. In sliding friction some edge sites will always be exposed, and so the friction of graphite under a vacuum is high. Vapors lower the friction by adsorbing selectively to the high-energy edge sites, saturating the bonds, reducing the adhesion, and therefore lowering the friction.

Because the reaction is controlled and initiated by the contact of a gaseous phase with the surface of the metal carbide structure, it allows monolithic parts with complex shapes, crevices, channels, intricate layered surfaces, holes, and other intricate surface morphologies to be treated. The process of the present invention is extremely advantageous compared to existing coating processes which generally require a "line-of-sight" to lay down the coating. In this way, not only carbide components or fibers can be coated, but also powders, whiskers, nanotubes, and platelets (not possible with current processes, CVD, PVD, and the like.

Moreover, the tailoring of the process by change of reaction gas composition, temperature, and time allows the production of carbon layers with varying structure, porosity, density, and other properties. Similarly, the process allows the control of carbon layer growth on the atomic level. It is to be noted that since the metal carbide itself is transformed into carbon, the original size and dimensions of the monolithic part are retained, allowing the part to be treated without loss of dimensional integrity, hence saving machining costs. Further, polishing of the finished part is unnecessary since the part will become "polished" in use to attain a constant coefficient of friction (after slight lowering) after a short use cycle.

It is evident that this process allows the use of the same reactor vessel, of almost any volume, for all types of carbon coatings desired. Since the process in its preferred embodiment takes place at atmospheric pressure, it is safer and cheaper than those processes (like hydrothermal etching) which take place at elevated pressures as well as those processes that take place under vacuum. Attention is also drawn to the fact that this process does not require plasma or other expensive high-energy sources. Means is provided for an environmentally friendly technology since the process can be performed close-circuit with all products reclaimed.

Thus the advantages of this invention include the production of carbon layers on a metal carbide for the purpose of achieving an adherent carbon layer with tailored structure and mechanical properties in an inexpensive, simple, environmentally friendly manner. Not only can the dimensional accuracy of the monolithic part be retained, but complex shapes of any size (nano to macro) can be treated in a way not possible by any existing method.

Experiments were performed in gas mixtures containing trace amounts up to 100% $Cl_2$ and 0 to 100% $H_2$ at temperatures from 100° C. to 4,000° C. Experiments were continued from between 1 minute to over a week depending on the reactivity of the metal carbide, temperature, pressure, time of reaction, halogen gas and hydrogen gas concentrations. Subsequently the reacted specimens were analyzed using optical and electron microscopy, Raman and FTIR spectroscopy, x-ray diffraction, energy dispersive x-ray analysis, nano-testing, and pin-on-disk wear testing. The kinetics of the halogenation (chlorination) reaction were determined at 1,000° C. for different gas mixtures and fit to a linear reaction rate equation.

By appropriate selection of temperature and gas composition, the structure of such carbon films can be controlled producing diamond, diamond like carbon, ordered and disordered graphite, active carbon, hydrogenated carbon, and other forms of carbons. Furthermore, the temperature and gas composition can be controlled to actually etch or "clean" the bulk carbide surface instead of producing a coating (useful in the electronic applications of SiC).

It was possible to control the above coating thickness, porosity, and morphologies by varying the $Cl_2$ to $H_2$ ratio, reaction temperature and time. Carbon surface layers from only a few microns to hundreds of microns thick were obtained. In fact, there is no limit to the thickness of the carbon coatings since the entire monolithic piece of metal carbide material can be transformed with sufficient time of reaction. In addition, the crystal size of the crystalline morphologies was also variable. It is important to note that this process is inherently different from other methods employed, in that the material (carbide surface) is actually transformed into a new material (carbon based) from the surface down into the material. This differs from "film" or coating applications which are applied or grown on top of the bulk material. The advantages of this method are the adherence of the film or coating. The interface is where the coating "grows into" the bulk monolithic, metal carbide port, providing excellent resistance to fracture and wear.

Pin-on-disk wear and friction testing was performed in humid air at room temperature. The friction force was monitored using a load cell, so that the friction coefficients could be determined continuously during testing at constant normal load and sliding velocity. Both the amorphous/disordered carbon and graphitic carbon greatly reduced the friction coefficients by up to seven times the untreated value. The coatings were extremely well adherent and wear-resistant showing virtually no substantial wear track after prolonged wear tests. For example a 50 micron graphitic coating had a wear track of less than 1 micron deep after tests of 50 meters with a ⅜ inch $Si_3N_4$ Ball, 5 N load and 0.0125 m/s linear sliding velocity. This low wear rate was present even under thousands of cycles, and was orders of magnitude less than the untreated values. The carbon coatings actually improved with the test duration, i.e., the coefficient of friction dropped with time, by virtue of wearing the microscopic carbon surface flat, with any displaced carbon that resulted from wear, filling microscopic low areas on the surface with time, thereby reducing friction.

Experimental Methods and Analysis Techniques

Experiments to produce carbon films by extraction of Si from SiC with chlorine were performed using commercially available monolithic β-SiC specimens (sintered Hexoloy™ SA, polished and unpolished) and CVD α-SiC. These samples were sectioned, cleaned, and placed in a sample holder. This was in turn suspended in the center of a fused silica reaction tube in the hot zone of a furnace. H2 and $Cl_2$ were supplied from premixed cylinders and the $Cl_2$ and $H_2$ concentrations were diluted with argon gas. Subsequently, the reacted specimens were analyzed using electron microscopy, Raman spectroscopy, and pin-on-disk tribology tests.

The Ramanscope 2000 micro-Raman spectrometer (Renishaw) was used with an Ar ion laser (514.5 nm) under variable magnification (50×–1000×) for analysis of carbon coatings.

This laboratory procedure allows one to determine the wear and coefficient of friction of materials during sliding using a pin-on-disk apparatus. Materials are tested in pairs: a "pin" with a radiused tip (usually a ball) and a "flat" (usually a circular disk). The test method can be found in ASTM G99, Section 3, Metals Test Methods and Analytical Procedures, Volume 3.02, Wear and Erosion; Metal Corrosion.

The pin specimen is pressed against the disk at a specified load (generally 5N in these experiments) and the sliding path is a circle on the disk surface. Friction coefficient versus cycles, time, or distance is the output. Wear results are reported as volume loss in cubic millimeters for the pin only during these experiments. This is due to the fact that the coating wear was so low that precise measurements could not be made. Wear can be a function of at least: applied load, machine characteristics, sliding speed, sliding distance, environment (relative humidity, temperature, gases present, etc.) and material properties. Test Parameters are: Load (N), Relative sliding speed (m/s or cm/s), Distance (m or km), Temperature (° C.), and Atmosphere. The standard test parameters used in this research were:

1. Load: 5 N (in variable test ranged from 1 to 16 N);
2. Relative sliding speed: 1.25 cm/s (in variable test ranged from 1.57 to 17.3 cm/s);
3. Sliding distance/Cycles: variable;
4. Wear track diameter: 6.0 mm;
5. Pin: 0.9525 cm, $Si_3N_4$ ball;
6. Temperature: room temperature (recorded); and
7. Environment: open air, variable relative humidity (recorded), one wet test was run.

During this testing, the following pin-on-disk test machines were utilized: CSEM Tribometer Pin on Disk Machine (CH-2000) and CSEM High Temperature Tribometer Pin on Disk Machine (CH-2007).

Results

When the sintered and CVD SiC were treated over a range of chlorine and hydrogen gas mixtures at 1,000° C. for various times, it was found that a carbon layer was formed. The layer was identified as highly disordered (amorphous) carbon with definite contributions from nanocrystalline or amorphous graphite (i.e., $sp^2$ bonding) by Raman spectroscopy, x-ray diffraction, transmission and scanning electron microscopy, and energy dispersive x-ray analysis. The kinetics of the chlorination reaction were determined at 1,000° C. for different gas mixtures and fit to a linear reaction rate equation. The carbon film thickness was between 2 μm and 100 μm depending on treatment conditions and time. This coating has never been worn down to the underlying SiC material in these experiments. In fact, the wear of the coating is so low that precise measurements are difficult.

Friction Coefficient Results

Figure 2:
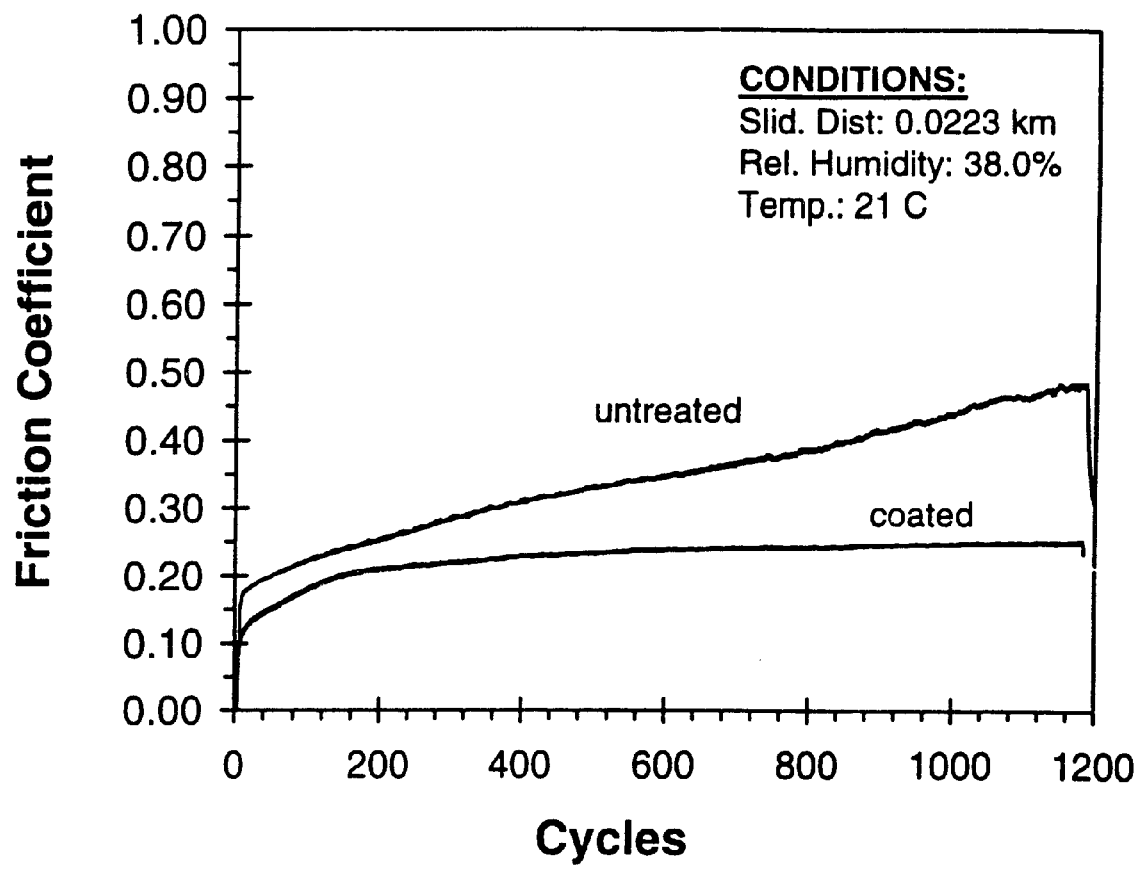
FIG. 2 is a graph showing friction coefficient vs. sliding distance for un untreated sample and sample treated in 2.77% $Cl_2$—1.04% $H_2$—Ar for 24 hours at 1,000° C.
Figure 3:
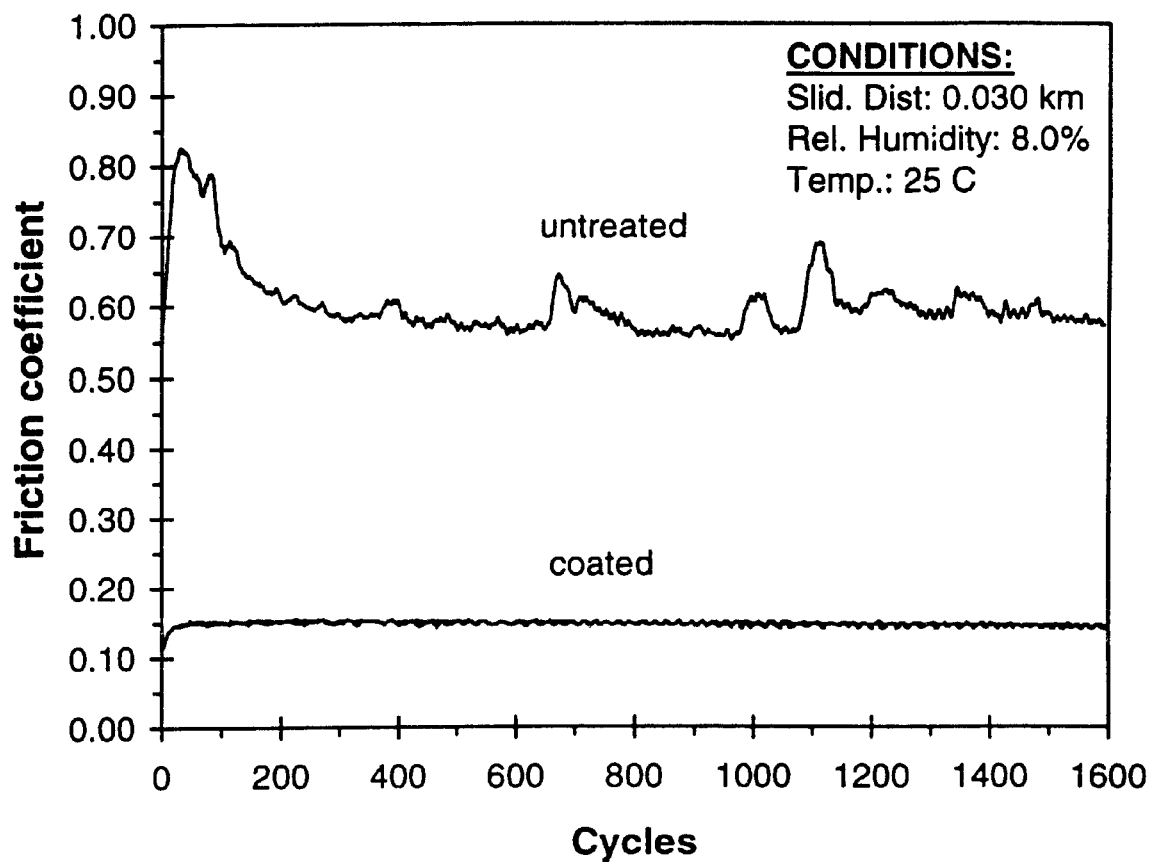
FIGS. 3 and 19 are graphs showing friction coefficient vs. sliding distance for an untreated sample and a sample treated in 2.77% $Cl_2$ $_{-1.04}$% $H_2$ —Ar for 19 hours at 1,000° C.

The tribology test results are most conveniently presented as graphical data in the form of a friction coefficient vs. sliding cycles plot. FIGS. 1, 2, and 3 are plots showing the "control" or untreated specimens vs. treated for sintered α-SiC (polished), CVD β-SiC, and sintered α-SiC (unpolished). These three samples are representative of the over 30 tribology tests run at the standard conditions stated in the experimental section.

FIG. 1 shows a friction coefficient of about 0.17 and steadily decreasing with cycles. The untreated SiC had a 0.4–0.5 friction coefficient.

Typical tribology test results of sintered α-SiC (substrate polished) samples (FIG. 1) showing friction coefficient vs. sliding distance for untreated sample and sample treated in 2.6% $Cl_2$—1.3% $H_2$—Ar for 24 hours at 1,000° C.

The coated CVD β-SiC specimen shows a reduction in the friction coefficient (FIG. 2), to about 0.24 from 0.4–0.5 (and steadily increasing) for the untreated CVD specimen.

Typical tribology test results of CVD β-SiC samples (FIG. 2) showing friction coefficient vs. sliding distance for an untreated sample and sample treated in 2.77% $Cl_2$—1.04% $H_2$—Ar for 24 hours at 1,000° C.

Finally, for sintered and unpolished α-SiC, the results are very similar to these seen for the other sintered SiC sample. FIG. 3 shows there is a reduction in the coefficient of friction from about 0.6 for the untreated specimen to 0.15 for the treated after 0.03 km. A longer test run was done, see FIG. 4, for 0.186 km (>8500 cycles) in which the coefficient of friction dropped to below 0.10 and continued to drop until the sample holder failed, releasing the specimen. From FIG. 4 it is clear that the carbon layer exhibits good adherence. No fracture or spallation of the carbon layer has been observed in any of the pin-on-disk tests on this material.

Typical tribology test results of sintered (unpolished) α-SiC samples (FIG. 3) show friction coefficient vs. sliding distance for an untreated sample and a sample treated in 2.77% $Cl_2$—1.04% $H_2$—Ar for 19 hours at 1,000° C.

Figure 4:
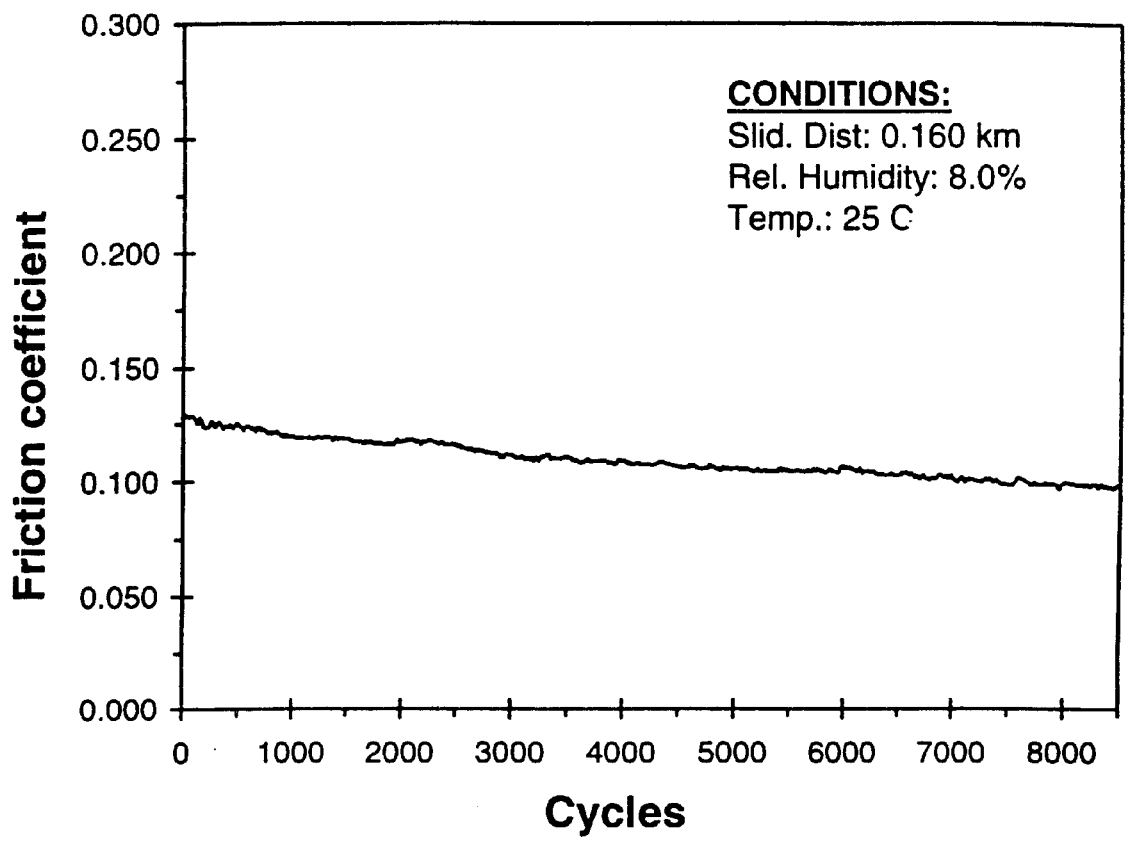
FIG. 4 is a graph showing the results of an extended tribology test of the treated sample of FIG. 3, showing continued reduction in friction coefficient, with time.

FIG. 4 shows an extended tribology test of the coated sample of FIG. 3, showing continued reduction in friction coefficient, with time.

Effects Of Loading and Speed

Figure 5A:
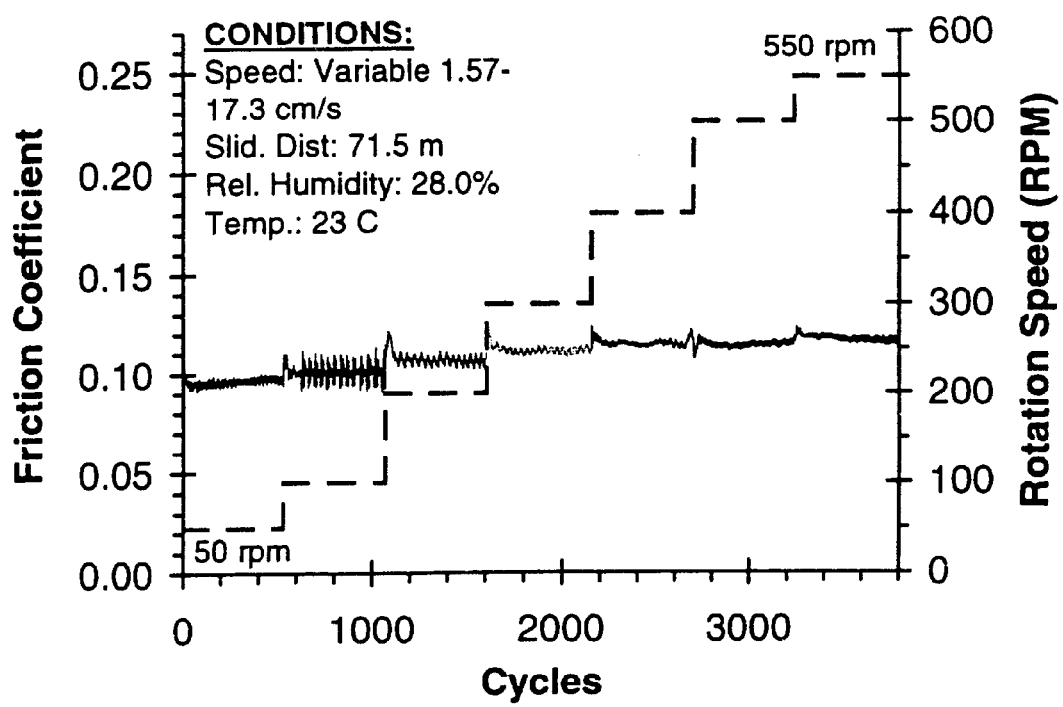
FIG. 5a is a graph showing the coefficient of friction results of a stepped speed pin-on-disk tribology test of a carbon layer of the present invention formed on -SiC, showing the relatively constant, low coefficient of friction at various speeds—even at 550 RPM.
Figure 5B:
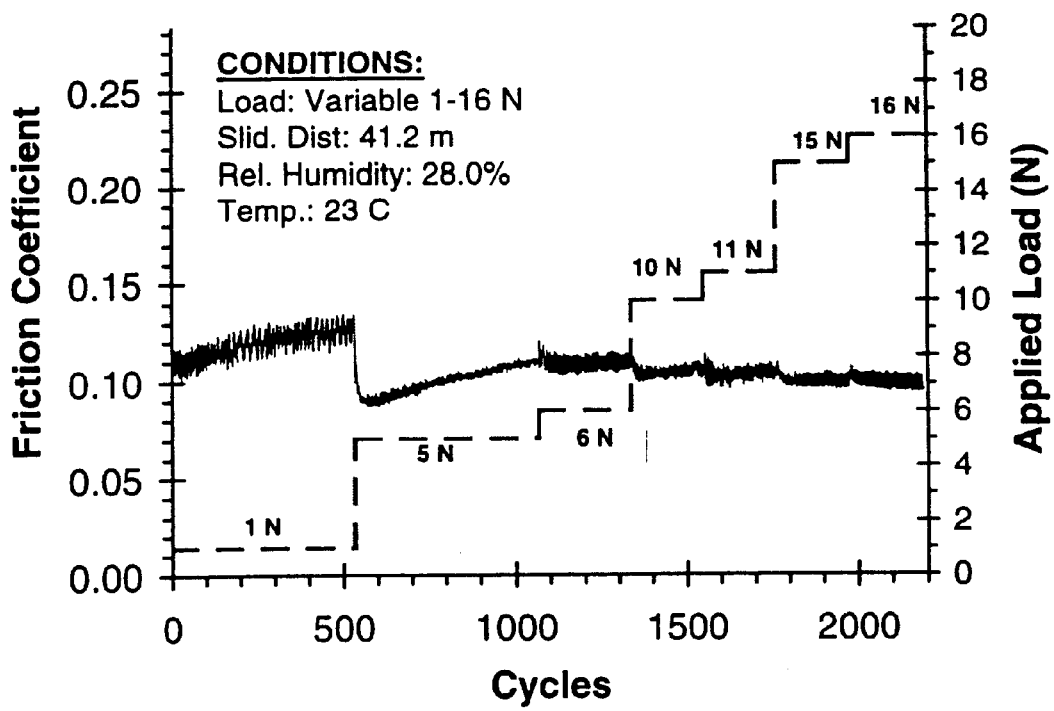
FIG. 5b is a graph showing the coefficient of friction-results of a stepped load pin-on-disk tribology test of a carbon layer of the present invention formed on -SiC, showing the relatively constant, low coefficient of friction at various loads—even at 16 N.

The load was varied from 1N to 16N in steps to investigate the effect of an increasing load on the friction coefficient of the carbon layer, see FIG. 5b. It is apparent that the load has little effect on the friction coefficient, in the studied range. The 1N load shows a higher friction coefficient and a more "noisy" signal. This is because the small forces provided under this low loading condition are approaching the measurement limit of the instrument. This can be expected due to the excessive vibration and poor seating of the pin and disk at such a low load. From 5N to 16N the friction coefficient is relatively steady at about 0.10.

The speed of rotation was also varied from 50 to 550 rpm (corresponding to 1.6 to 17.3 cm/s linear velocity) to show the effect of speed on the friction coefficient of the carbon layer, see FIG. 5a. Again, there was little effect on the friction coefficient, which was approximately 0.10 to 0.12 over the tested speed range.

Effects of Polishing Carbon and Water Addition

Figure 6:
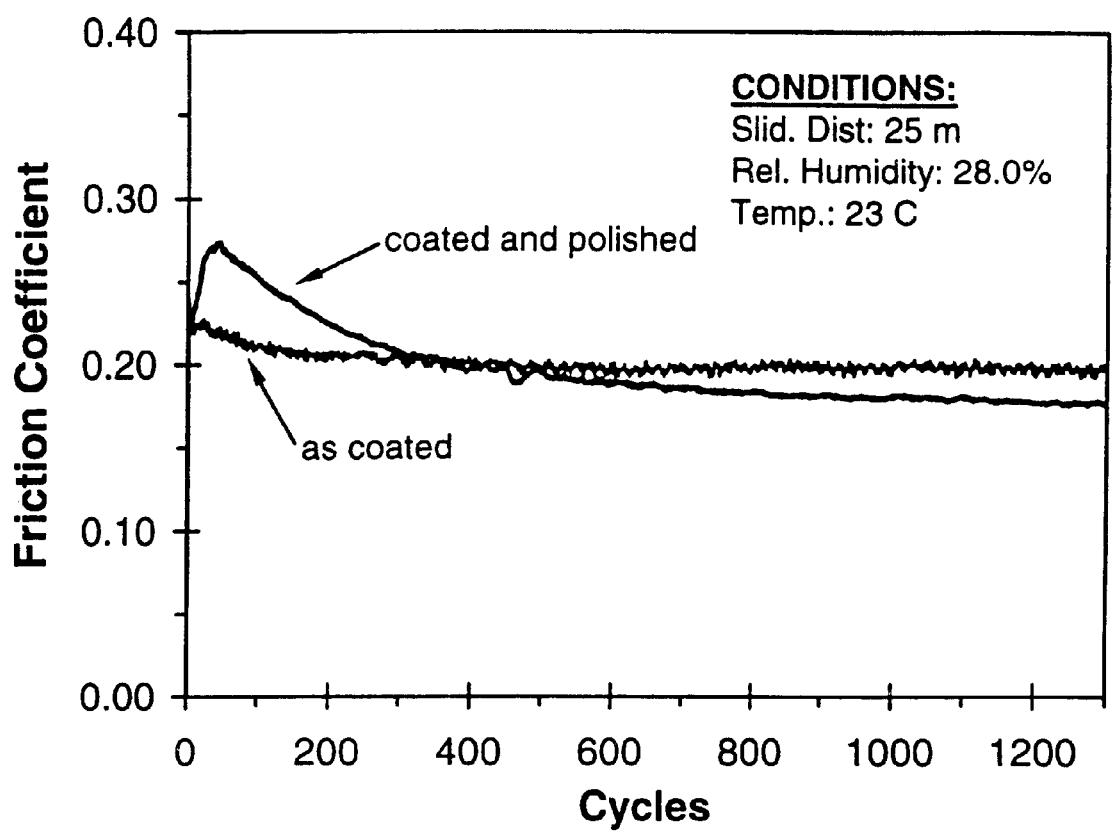
FIG. 6 is a graph showing the effects of polishing carbon layer on friction coefficient for sintered SiC treated in 3.55 $Cl_2$—Ar for 19 hours at 1,000° C.

To see if the initial surface roughness of the carbon layer had an effect on the friction coefficient, a sintered SiC sample treated in 3.5% $Cl_2$—Ar for 19 hours at 1,000° C. was tested in the unpolished and polished (to 0.15 micron) condition, see FIG. 6. There was little effect on the observed friction coefficient except during the first 250 cycles.

Figure 7:
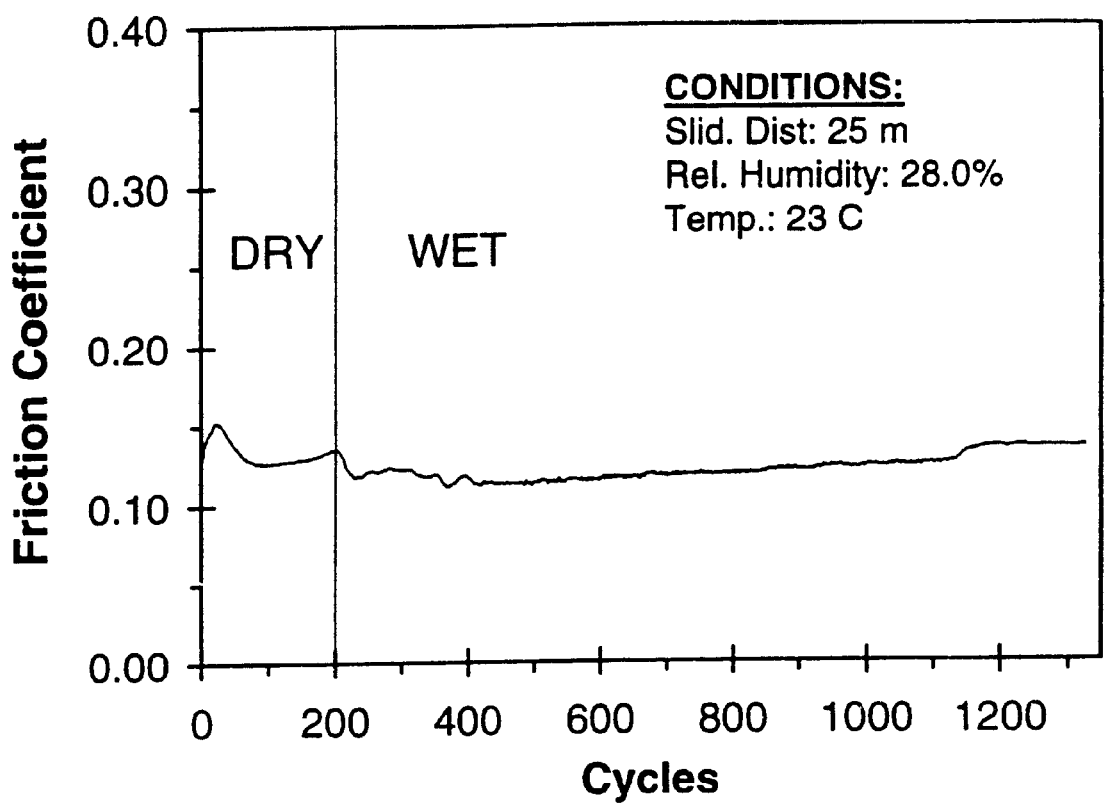
FIGS. 7 and 22 are graphs showing the effect of immersing the formed carbon layer in water during a $Si_3N$ pin-n-disk friction test. The sintered SiC sample was treated in 3.5% $Cl_2$—Ar for 41 hours at 1,000° C.

To establish if the carbon layer responded differently when tested dry versus wet, a sintered SiC sample was treated in 3.5% $Cl_2$—Ar for 41 hours at 1,000° C. and tested dry for 200 cycles at which point it, along with the test pin, was immersed in distilled (deionized) water at 23° C., see FIG. 7. The effect was a very small decrease in friction coefficient. This could have been due to a water layer forming between the pin and disk in effect allowing a slight hydroplaning action.

Structure of Carbon Layer, Wear Surfaces and Wear Debris

Figure 8B:
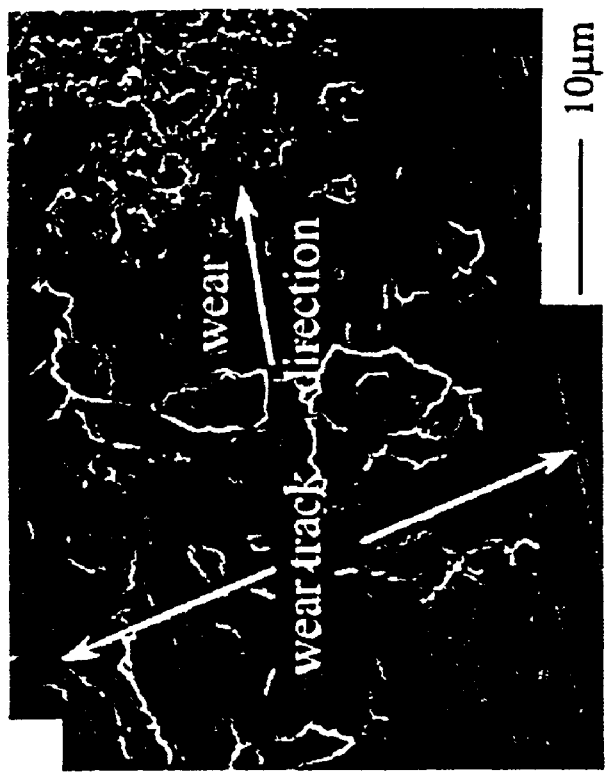
FIGS. 8a and 8b are SEM micrographs of 8a—an unworn area of sintered SiC sample treated in 3.5% $Cl_2$—Ar for 38.5 hours at 1,000° C., and 8b—showing the centerline of wear track of a sample after the treatment seen in FIG. 5.
Figure 8A:
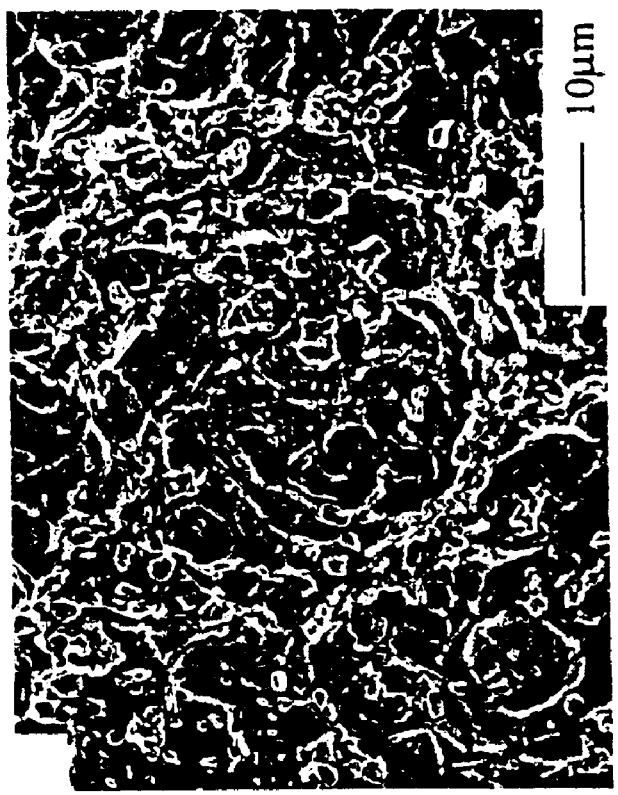

FIG. 8a shows the treated, unworn carbon layer surface. FIG. 8b is a micrograph of the same sample after wear testing, showing the centerline of the wear track (wear direction is left to right). It is apparent that there is drastic smoothing of the surface as the wear test progresses. The pits, bumps, cracks, etc. have been flattened out or filled, resulting in a much smoother surface that still shows some sign of the original topography.

Figure 9B:
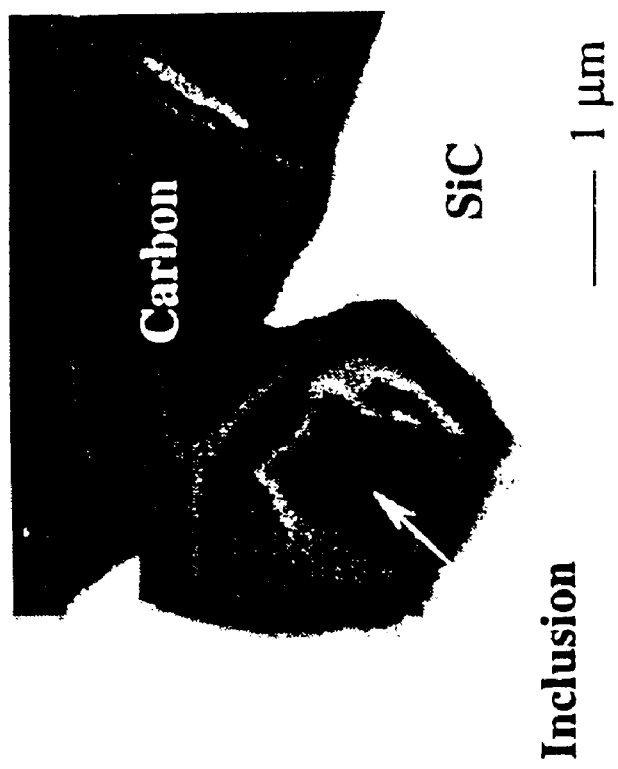
FIGS. 9a and 9b are SEM micrographs of fracture surface, showing carbon/SiC interface for 9a—CVD β-SiC sample treated in 2.77% $Cl_2$—1.04% $H_2$—Ar for 24 hours at 1,000° C.); 9b—SiC/carbon interface (fracture surface) showing carbon growth around the inclusion and excellent bonding between surfaces for SiC sample treated in 3.5% $Cl_2$—Ar for 53 hours at 1,000° C.
Figure 9A:
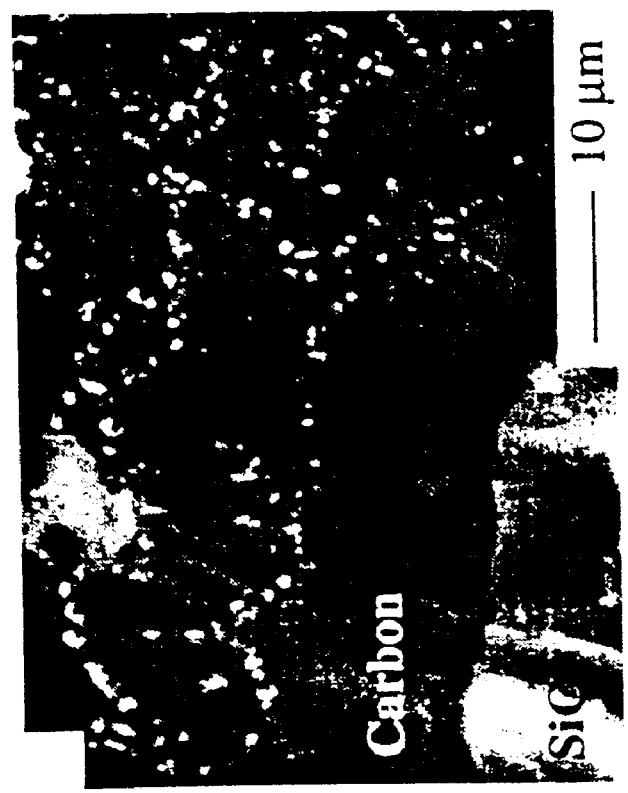

FIG. 9a is a fracture surface showing the cross-sectional view of the carbon layer over the CVD β-SiC substrate. One can see the excellent bonding between the carbon and SiC as the fracture features are seamlessly continued across the interface. Likewise, FIG. 9b is a fracture surface showing the cross sectional view of the carbon layer over the sintered α-SiC substrate. In addition, there is an inclusion in the center of the micrograph which has been surrounded by the carbon layer as the carbon/SiC interface progressed through the substrate. Again, it is apparent that the interface has a tight bond as seen by the fracture patterns across the interface.

Figure 10B:
FIGS. 10a, 10b and 10c are SEM micrographs showing wear track extrusions extended over a pit in the wear track on a sintered SiC sample treated in 3.5% $Cl_2$—Ar for 38.5 hours at 1,000° C.
Figure 10A:
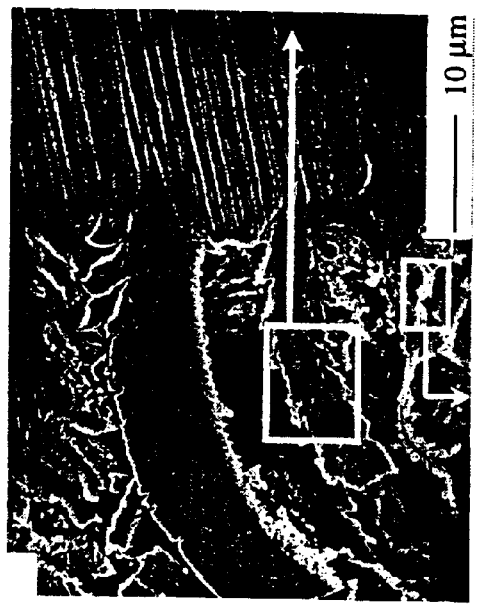
Figure 10C:
Figure 11B:
FIGS. 11a through 11d are SEM micrographs showing wear track extrusions extended over the outer edge of the wear track of a sintered SiC sample treated in 3.5% $Cl_2$—Ar for 38.5 hours at 1,000° C.
Figure 11D:
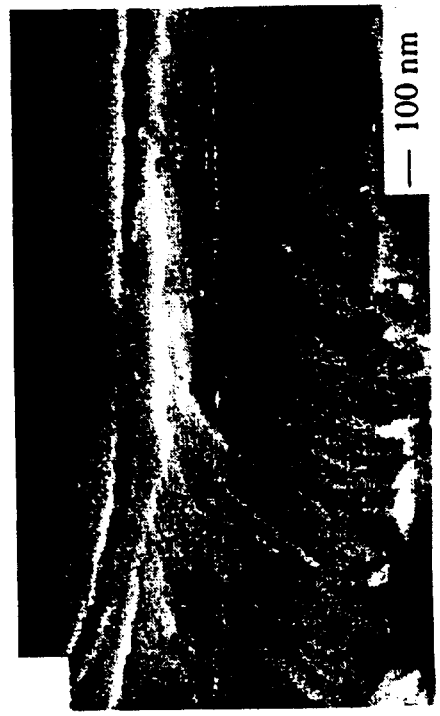
Figure 11A:
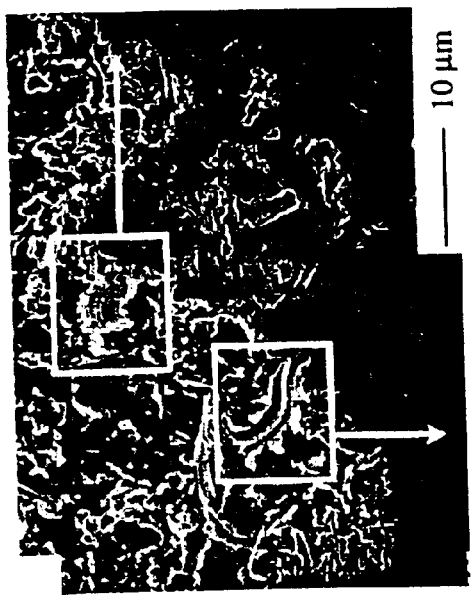
Figure 11C:

FIG. 10 is a series of SEM micrographs showing wear "extrusions" protruding over a pit in the wear track. The wear direction in FIG. 10a is from the right to the left. One can see ploughing marks in this orientation. When the extrusions are examined under higher magnification in FIG. 10b and 10c, one can see that they are not "chips" or "turnings" from a machining action of the pin, it is theorized that the extrusions are formed by cyclic plastic deformation and ploughing of the carbon layer. If there was no pit on the surface, the extrusions would not be formed, but the surface would be flat as seen in FIG. 8b.

FIG. 11 shows additional extrusions with the exception that they overhang the outer edge of the circular wear track instead of a pit within the wear track. Again, FIG. 11a is a micrograph showing many such extrusions with higher magnification micrographs of individual extrusions in FIG. 11b and 11c. FIG. 11d is a very high magnification micrograph of the center of the extrusion seen FIG. 11c. Here one can see the banded structure which most likely formed from the cyclic deformation caused by the pin ploughing over the carbon surface.

Clearly, from FIGS. 1–3, the carbon layer formed has excellent frictional properties regardless of the type of SiC used as the substrate, sintered α-SiC or CVD β-SiC. It should be noted that when the sintered SiC itself was polished that the untreated friction coefficient was lower than the unpolished sintered SiC (0.40 versus 0.60) as would be expected. However, this polishing step done before treatment to form the carbon layer had little or no effect on the properties of the carbon layer. This is explained by smoothing of the surface carbon coating under frictional load, as shown in FIG. 8b.

The friction coefficient actually improved with testing probably due to a further smoothing of the carbon layer from the as treated condition seen in FIG. 8a to the worn condition seen in FIG. 8b.

The effects of polishing the carbon layer (vice the SiC substrate as before) can be seen in FIG. 6, where there is very little change in the friction coefficient profile with cycles except during the first 200 cycles. It is suggested that the polished sample, initially had a slightly higher coefficient of friction due to the extra time needed to establish a carbon transfer layer on the $Si_3N_4$ pin. Once this layer was established, there was little difference in the layers friction coefficient of about 0.20.

As was shown in FIG. 10 and FIG. 11, the major discernible feature of the wear track was the "extrusions" which were seen overhanging pits in the wear track or at the outer periphery of the track. The fine details of FIG. 10b and FIG. 11d showing the ridges or layered structure of these extrusions suggests that these were built up over many cycles by a plastic deformation of the carbon layer. Normally the rough as-treated surface of the carbon layer is flattened out by the wear process as seen in FIG. 8b. However, when there is space for the carbon to flow into (as over a pit or on the edge of the wear track) these extrusions are formed and not flattened over or smoothed out by successive cycles. In effect, these wear features are an indication that the carbon layer can have plastic properties under loading (specifically wearing conditions) vice a brittle cracking and fracture behavior. The layer is "self-adjusting" to the loading geometry and conditions resulting in a smooth sliding surface with a low friction coefficient. Therefore, it is relatively insensitive to load, speed, water, initial surface roughness, or choice of substrate SiC.

Figure 12:
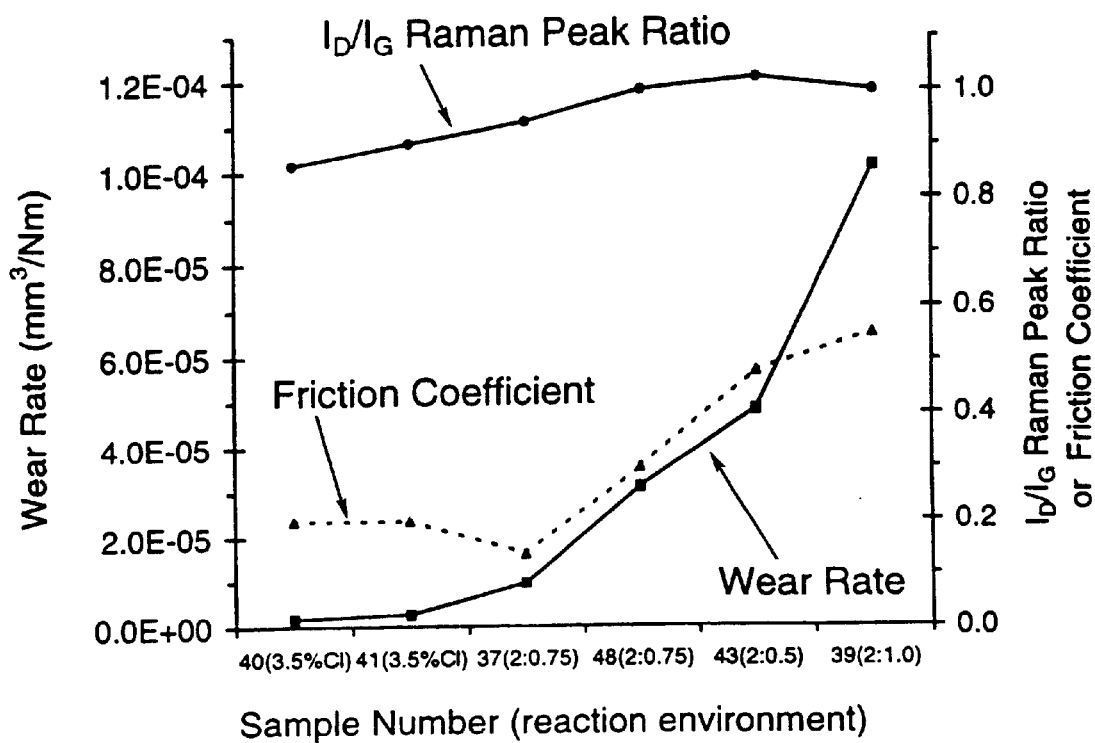
FIG. 12 is a graph showing the coefficient of friction, wear rate, and $I_D/I_G$ ratio for 0.03 km wear tests, the sample numbers and $Cl_2$ concentrations are shown along the x-axis (either $Cl_2$ or $Cl_2:H_2$ ratio)

Because of the complicated nature of tribological tests and the many variables involved in such tests, it is prudent to compare results between tests that were conducted under similar conditions. For this reason, all the tests that were conducted under the same speed, environment, and wear distance of about 0.030 km were grouped and various parameters were plotted in FIG. 12. The Sample Number is along the x-axis along with the composition of the reaction gas mixture (either $\%Cl_2$ or $C_2:H_2$ ratio).

As one would expect, as the friction coefficient increases so does the wear rate (of the pin). As one can see, the wear rate is normalized for both applied load (N) and distance (m). The samples that had a coefficient of friction between 0.1 and 0.2 resulted in extremely low wear rates of 1.00E–05 $mm^3/Nm$ or less. Although sample #37 shows a bit of a reverse trend, it is within the accuracy of these tests.

Next the $I_D/I_G$ ratio of the same samples was plotted in parallel with the wear rate. This shows a strong dependence of the Raman peak ratio with the wear rate, in that as the $I_D/I_G$ ratio increases so does the wear rate.

Figure 13:
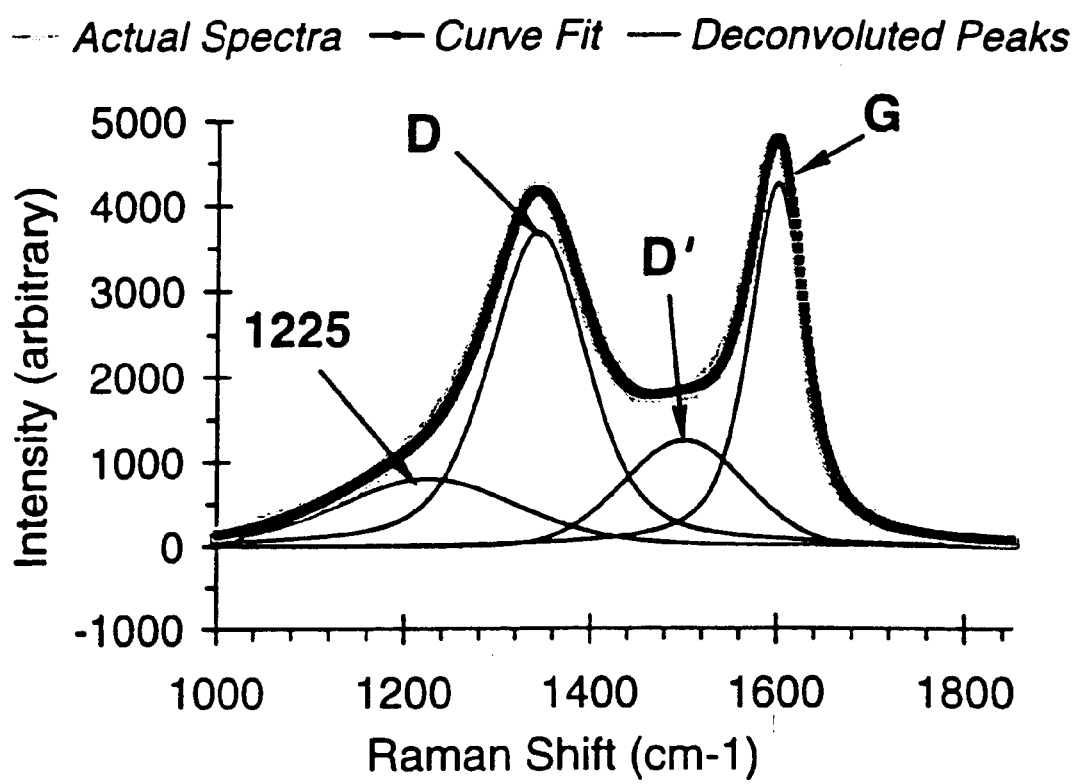
FIG. 13 is a graph showing deconvoluted Raman spectra using four bands, with broad bands manually place. The sintered SiC sample was treated in 3.5% $Cl_2$ for 19 hours at 1,000° C.
Figure 14B:
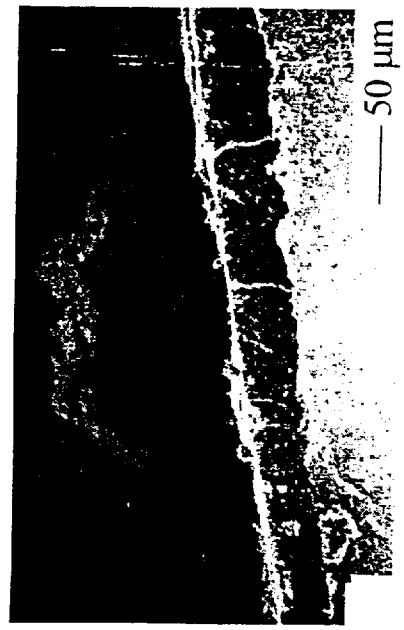
FIGS. 14a, 14b, 14c and 14d are SEM micrographs of the surface of a typical sintered α-SiC(B) sample treated in 3.5% chlorine at 1,000° C. for 19 hours showing: 14a—cracked, loose top carbon layer; 14b—cross-sectional view of adherent carbon sub-layer below it; 14c—higher magnification SEM micrograph of the adherent carbon layer fracture surface; and 15d—and a Raman spectrum of carbon layers and untreated SiC (G=graphite, D=disorder induced band of graphite)
Figure 14A:
Figure 14D:
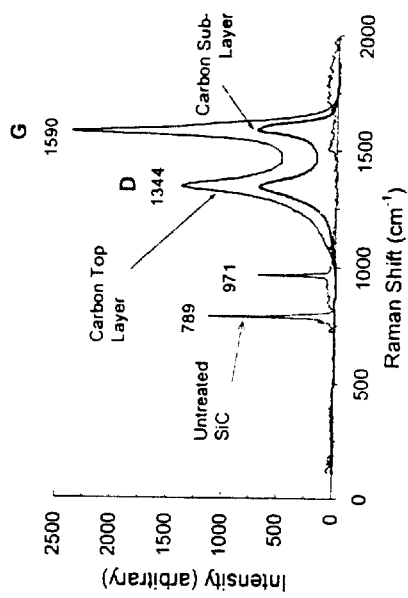
Figure 14C:
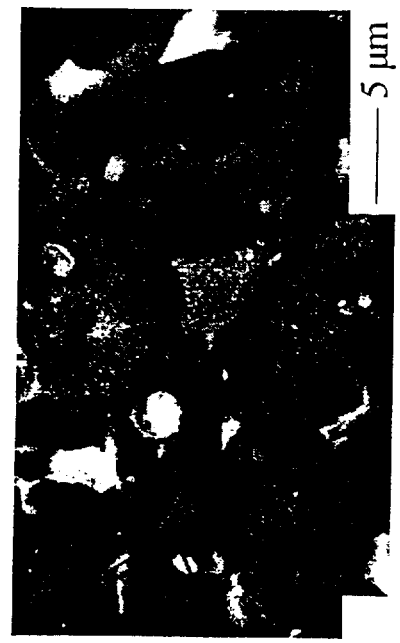

To explain this trend, one must look at a typical Raman spectra of disordered or amorphous carbon. FIG. 13 is such a spectra along with its deconvolution spectra. The G band is present in crystalline graphite with an increasing intensity of the D band as disorder increases.

FURTHER EXPERIMENTAL

Further experiments were performed using commercially available monolithic SiC specimens. Sintered Hexoloyl™ SA α-SiC was obtained from two separate sources, called SiC (A) and SiC (B). CVD β-SiC, called SiC (C), was also tested. In addition, several sintered α-SiC samples from Elektroschrnelzweik Kempten (ESK), Germany, called SiC (D), were used for comparative experiments. The selected samples provide a good representation of SiC ceramics, including cubic (3C or β) and hexagonal (6H and other α-SiC polytypes) structures, pure SiC and materials with sintering additives. These samples were sectioned into disks 16 mm in diameter and 1 mm thick. The disks were cleaned ultrasonically, rinsed in acetone, and placed in a platinum foil or quartz sample holder. This was in turn suspended via a platinum or silica wire connected to a fused silica rod in the center of a fused silica reaction tube in the hot zone of a furnace.

The SiC was exposed to flowing gas mixtures of Ar, $H_2$ and $Cl_2$. $H_2$ and $Cl_2$ were supplied from premixed cylinders (3.5 vol. % in argon gas). These gases were passed through either anhydrous $CaSO_4$ or concentrated sulfuric acid, $H_2SO_4$, to remove water vapor and mixed in a packed (glass bead) mixing column. All non-reactive gases were ported through Pyrex glass and Tygon™ flexible tubing and used purified n-butyl phthalate (Dibutyl Phthalate) as the liquid for flow indication and pressure measurement. The $Cl_2$ gas was ported through Pyrex glass and Teflon PTFE tubing and used sulfuric acid as the liquid for flow indication and pressure measurement. All flow rates (both argon purge and reaction gas mixtures) were metered into the furnace at a superficial linear velocity of 1.5 cm/s in the reaction tube at reaction temperature and atmospheric pressure.

To begin each experimental run, argon gas was purged through the reaction tube for at least 30 minutes. The furnace was then raised to operating temperature at a rate of 6.5° C./minute, and once stable, the reaction gas mixture was introduced for the specified time. Over 50 experiments were performed in gas mixtures containing various amounts of $Cl_2$, $H_2$, and Ar at temperatures from 700° C. to 1,000° C. However, since experiments at 700–800° C. produced very thin films, only results of the experiments at 1000° C., which provide the highest growth rate, will be described.

Experiments were continued from between 30 minutes and several days depending on the reactivity of the environment. At the end of each experimental run, the furnace and reaction gas mixture was secured and an argon purge was initiated through the reaction chamber during the cool down period. Subsequently, the reacted specimens were analyzed using optical and scanning electron microscopy (JEOL 6320F field emission SEM), energy-dispersive spectroscopy (EDS), x-ray diffraction (XRD), and Raman spectroscopy. A Nano Indenter XP (MTS) equipped with a Berkovich indenter (diamond pyramid) was used to measure the hardness and Young's modulus of the coating. The tribological properties were determined in pin-on-disk tribology tests described elsewhere.

Raman microspectrometer Renishaw model 2000 with an Ar+ laser (excitation wavelength of 514.5 nm) and a diode laser (782 nm) was used for characterization of the carbon. The Raman spectra obtained were deconvoluted into individual bands that contribute to the experimentally obtained spectra. This was done with the aid of a spectral analysis software GRAMS 32. It was decided to be as conservative as possible when curve fitting the data, i.e., a minimum number of assumptions were made and an attempt to fit the data with the least number of deconvoluted bands that made good scientific sense was always applied. The correlation coefficient ($R^2$) value was used as a general indication of the curve fit and was considered acceptable at values of 0.98 to 1.02. The total data points fitted was usually about 1,200 per curve.

Structure and Composition
Samples Treated with Chlorine:

Samples that were treated with chlorine gas (3.5 vol. % $Cl_2$—balance argon) all developed a surface layer of carbon.

XRD analysis of the samples treated in chlorine showed the first seven most intensive XRD peaks for SiC due to the substrate, as well as the first four peaks for hexagonal graphite. This demonstrates the formation of graphitic carbon after chlorination.

Figure 15B:
FIGS. 15a and 15b are SEM micrographs showing: 15a—the cross-sectional view of 200-μm thick carbon layer from treating sintered α-SiC in 3.5% $Cl_2$ balance Ar for 24 hours at 1,000° C.; and 15b—fracture surface exhibiting excellent adherence of the carbon layer for a sample treated in 2.77% $Cl_2$—1.04% $H_2$—Ar for 24 hours at 1,000° C.
Figure 15A:
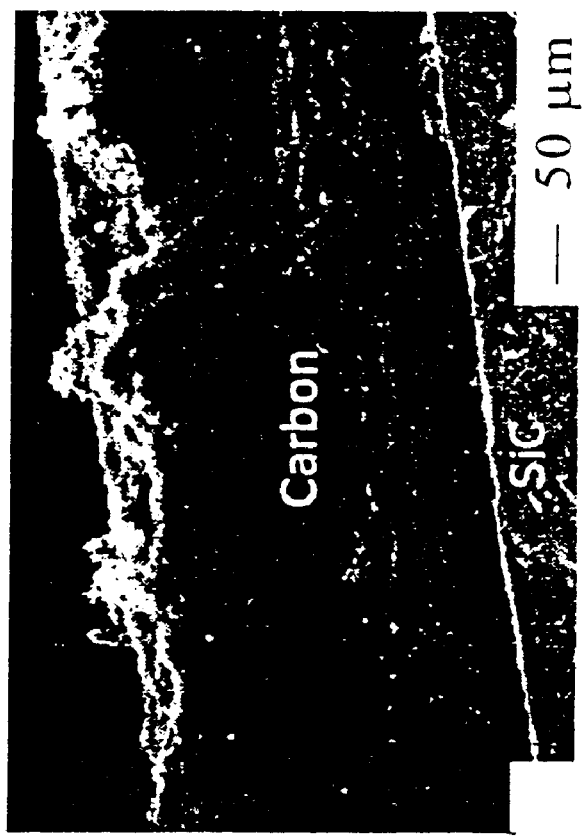
Figure 16B:
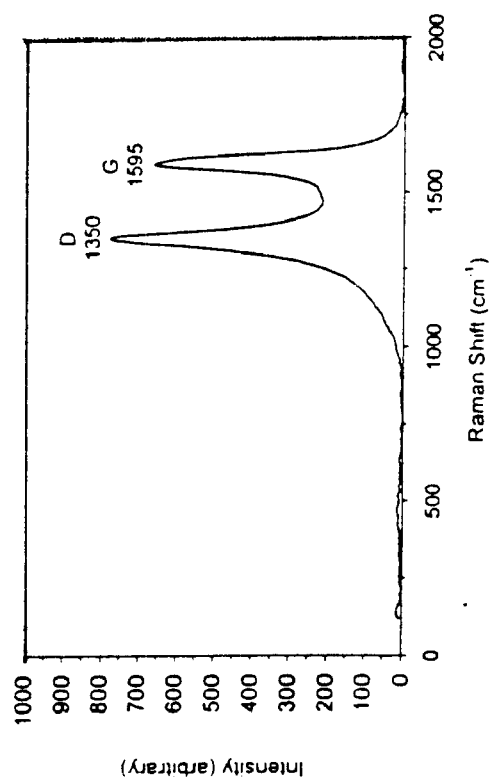
FIGS. 16a and 16b are SEM micrographs of a fracture surface showing the carbon layer over the SiC substrate. The sample was: 16a—sintered α-SiC treated in 2.77% $Cl_2$= 1.04% H2 (balance Ar) for 30 hours at 1,000° C.; and 16b—a typical Raman spectrum of carbon layer produced with hydrogen present in the reaction gas (b)
Figure 16A:
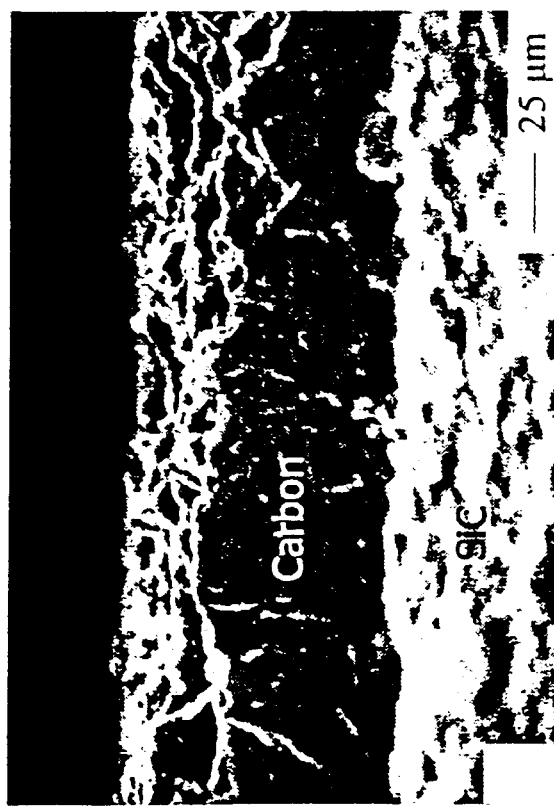

FIG. 14 shows the structure of the carbon layers formed on sintered SiC(B) after treatment in 3.5%$Cl_2$—Ar for 19 hours at 1,000° C. FIG. 14*a* shows the exterior surface of the specimen with a loose, non-adherent layer of graphite. This top layer was powdery and loosely attached in almost all cases and could be easily removed with a 5-minute ultrasonic bath in water or acetone. FIG. 14*b* shows a cross sectional view of a typical fracture surface of the specimen. The convoluted shapes in the top of the micrograph are the non-adherent graphite, the bright phase at the bottom is SiC, and the dark band between them is the dense carbon layer. This carbon could not be separated from the SiC by ultrasonic cleaning or any other technique, and no spallation or separation of this layer from the SiC was detected when the specimens were fractured. This layer was optically black. The microstructural features of the carbon layer (FIG. 14*c*) are similar to those of the SiC substrate. Traces of the SiC grain boundaries and inclusions are apparent in the micrograph, although the SiC has been converted completely into carbon as shown by the Raman spectroscopy analysis. Typical Raman spectra of the top carbon layer and the adherent film can be seen FIG. 14*d* along with the spectrum from the untreated specimen showing transversal (TO) and longitudinal (LO) optical phonons of SiC at 789 and 971 cm$^{-1}$, respectively. Raman spectra of graphite include a G band at 1582 cm$^{-1}$, and several other features associated with disorder in the structures. The most prominent of these is the D band, which occurs at about 1350 cm$^{-1}$, for the 514.5 nm excitation. The top layer and the adherent layer produce similar Raman spectra, but with a higher degree of graphitization in the top layer as demonstrated by a higher intensity of G band. It could have $I_{D/IG}$ ratios as low as 0.2–0.3, which are comparable to ordered polycrystalline graphite. We suggest that the upper layer is formed by graphitization of the lower carbon layer due to its interaction with the environment during the chlorination process leading to its cracking and fragmentation. Transport of carbon via gas phase results in subsequent formation of graphite crystals by surface transport reactions. Improvement of the size and ordering of graphite crystals when small amounts of hydrogen were added stimulating the surface transport on carbon supports this hypothesis. The adherent layer always had a high $I_D/I_G$ ratio indicative of a more disordered carbon type with its increased cross bonding between crystallite plates. This would explain the denser, harder structure of the adherent layer. It was grown to thickness more than 200 μm (FIG. 15*a*) and did not delaminate.

Samples Treated with a Chlorine/Hydrogen Gas Mix

When relatively small amount of hydrogen gas was added to the reaction gas mixture (2.98% $Cl_2$—0.74% $H_2$—Ar), the coatings obtained were similar in appearance and XRD spectra to those on samples treated in chlorine alone. When Raman line scans were done across the coating cross section, there was no significant variation in spectra from the carbon/SiC surface to the exterior surface and the sub-layers had a similar Raman signature in Ar—$Cl_2$ and 2.98% $Cl_2$—0.74% $H_2$—Ar. The loosely adherent surface layers formed in $Cl_2$—$H_2$—Ar mixtures were generally more crystalline than those formed in Ar—$Cl_2$, possibly due to enhanced surface diffusion in the presence of hydrogen.

Figure 17:
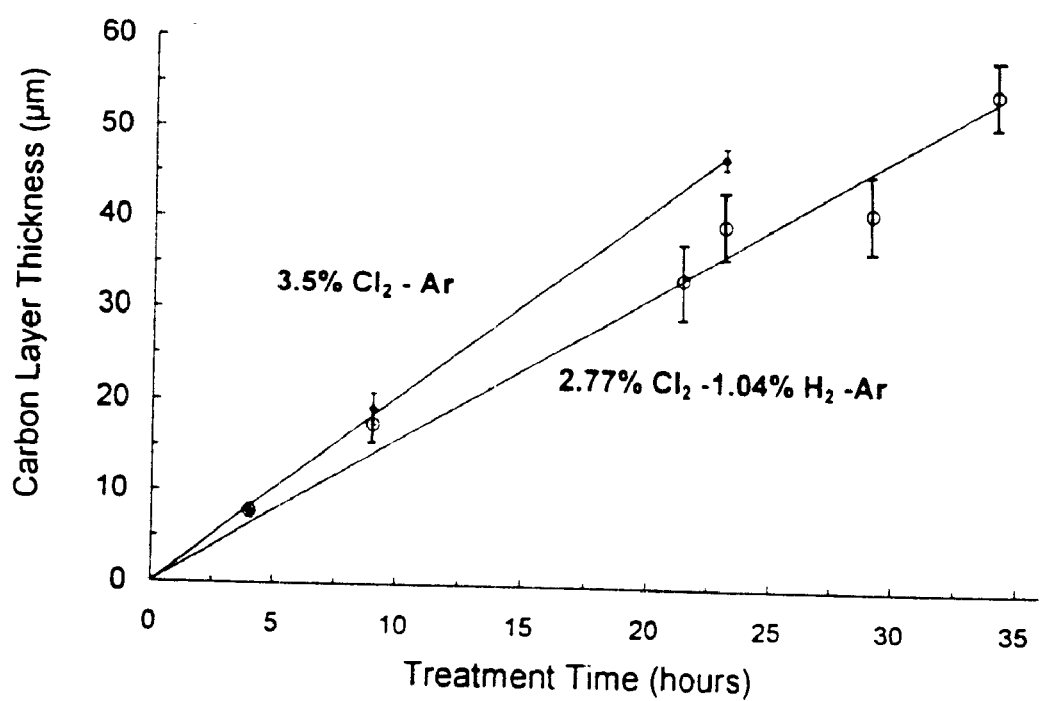
FIG. 17 is a combined kinetics data plot for chlorine and 2.77% $Cl_2$—1.04% $H_2$—Ar at 1,000° C.

The addition of 1.04% hydrogen to the gas mixture slows the reaction by about 22% (FIG. 17). The chlorine content of the hydrogen containing gas mixture was 30% lower than that in the gas mixture without hydrogen, and if the reaction between hydrogen and chlorine to form HCI reaches equilibrium the chlorine content will be 50% lower than that in the chlorine free gas mixture. Therefore, the effect of hydrogen addition on the kinetics of the carbon formation is smaller than would be expected based on the chlorine content of the gas mixture.

Increasing the hydrogen content of the gas mixture so that the ratio of chlorine to hydrogen was less than 2:1 (2.6% $Cl_2$—1.3% $H_2$—Ar) had a dramatic effect on the kinetics of the reaction. Gas mixtures with a ratio of chlorine to hydrogen of 2:1 appeared to represent a tipping point between conditions that produced rapid carbon growth and slow film formation. Assuming the formation of HCl reaches equilibrium with $H_2$ and, $Cl_2$, the chlorine content of the 2:1 gas mixture is approximately ⅓ of that in the hydrogen free gas mixture. Based on the results presented in FIG. 17, this would not be expected to produce a drastic decrease in the rate of the reaction. Based on thermodynamics, one would not expect a substantial decrease in the chlorine potential of the gas mixture until the ratio of chlorine to hydrogen is reduced to 1:1, which would lead to complete consumption of pure chlorine and formation of HCl. Chlorination reactions could also be inhibited by the formation of a passive oxide film, however, the addition of hydrogen to the gas mixture would be expected to reduce the oxygen potential, making such reactions unlikely. Thus, formation of a dense carbon structure inhibiting the chlorination process is assumed.

Effect of Oxygen Contamination

Figures 18A, 18B:
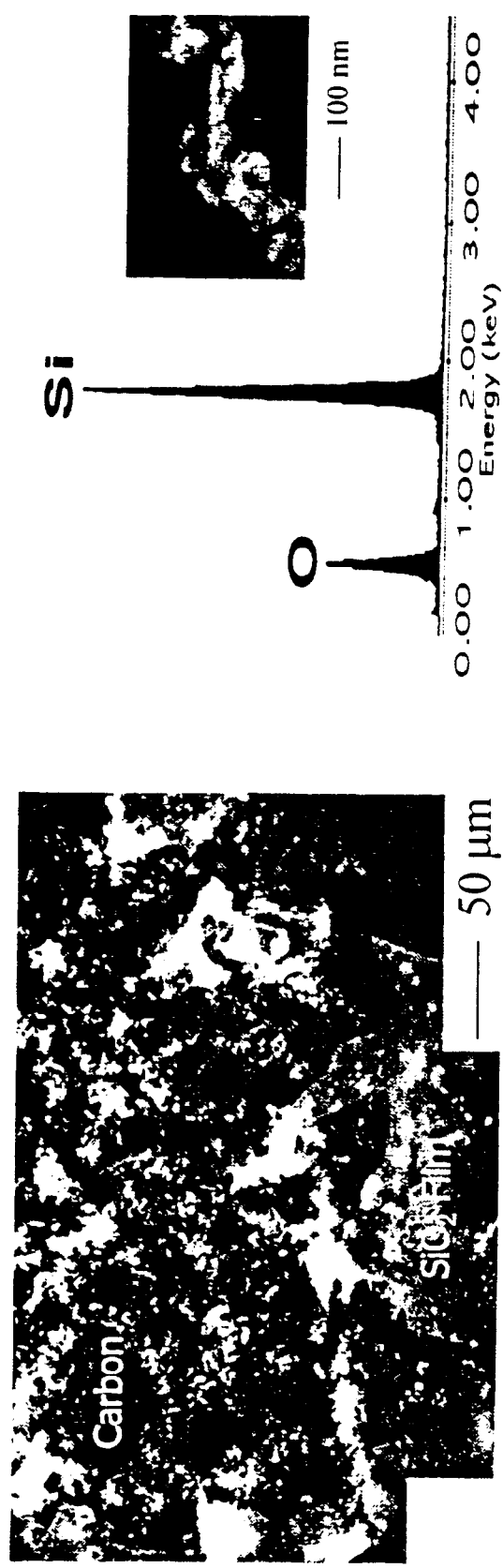
FIGS. 18a and 18b are SEM micrographs of: 18a—a translucent $SiO_2$ film (lower half of figure) which can be seen over the surface of the top carbon layer; and 18b—its EDS spectrum. The sample was treated in 2.6% $Cl_2$—1.3% $H_2$—Ar at 1,000° C. for 22 hours. The insert in FIG. 18b shows the fine structure of the fibrous silica film.
Figure 19:
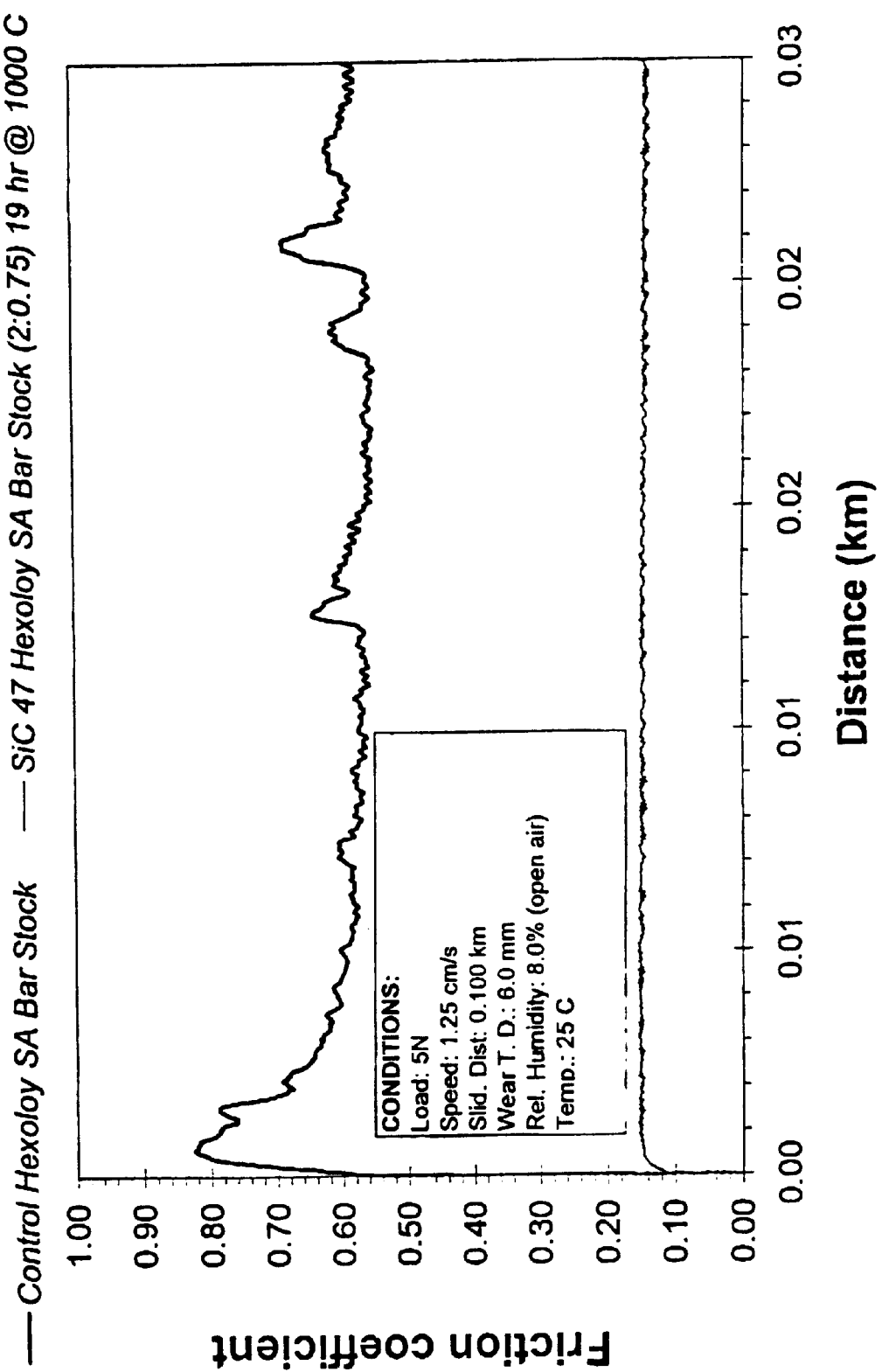
Figure 20:
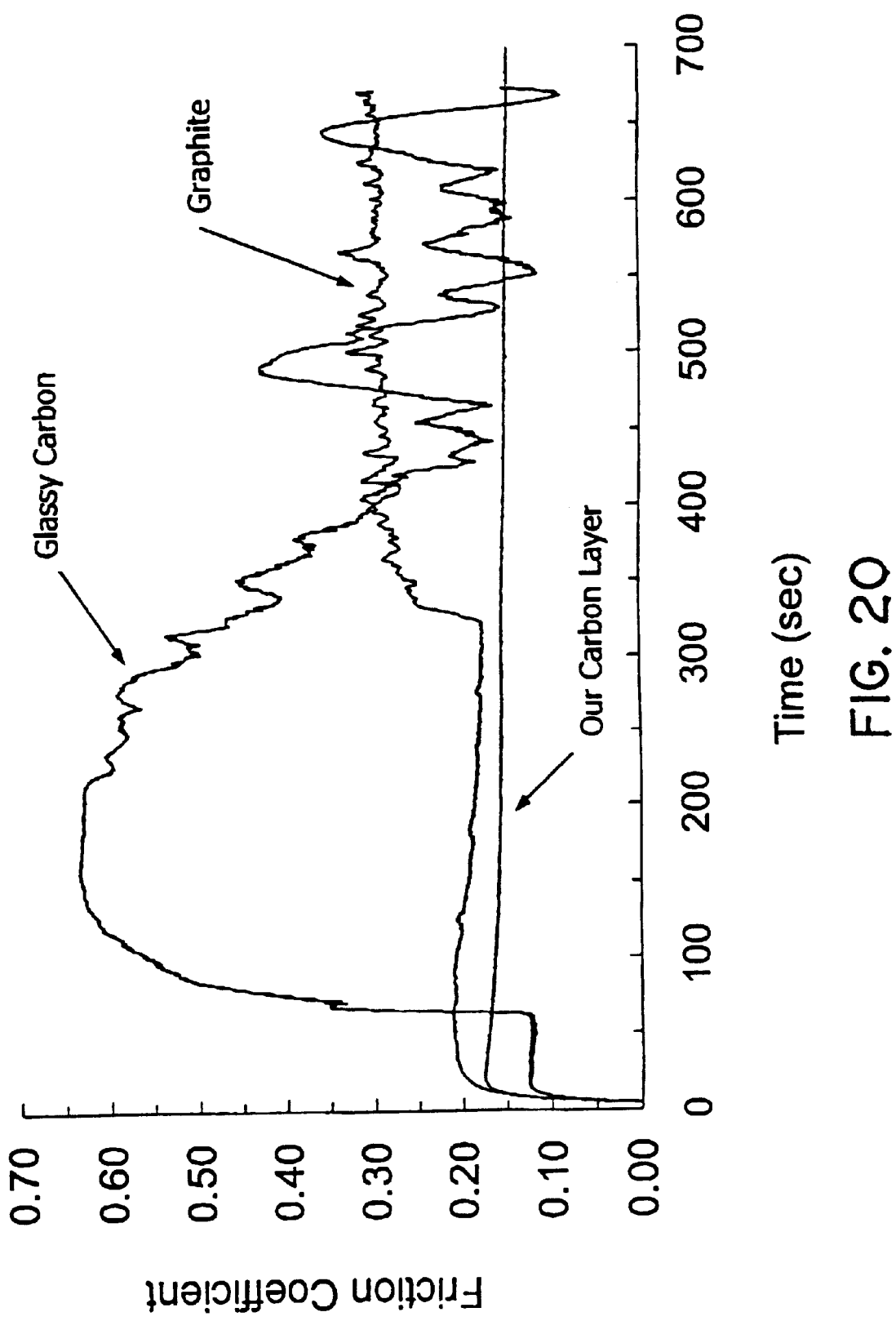
FIG. 20 is a graph showing the substantially varied coefficient of friction of graphite and glassy carbon vs. $Cl_2$—treated SiC, having a substantially pure carbon layer and essentially constant coefficient of friction that decreases slightly with wear in a pin on disk tribotest in dry nitrogen (0.0% relative humidity)
Figure 21:
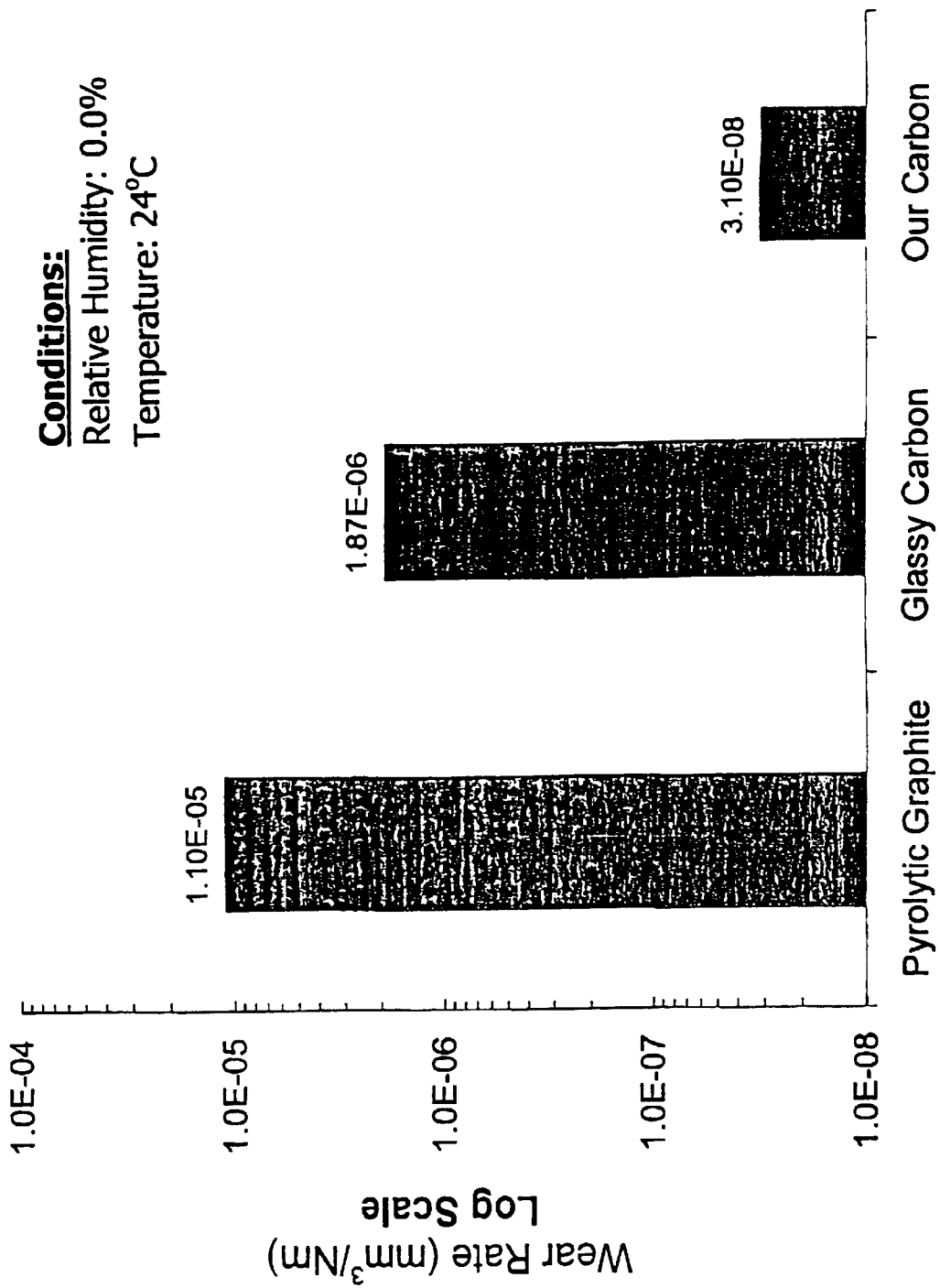
FIG. 21 is a graph showing the wear rate in dry air showing that while the presence of oxygen increases the wear rates for pyrolytic graphite and glassy carbon, due to oxidation, the treated (carbon coated) silicon carbide made in accordance with the present invention maintains a low wear rate in the presence of oxygen.
Figure 22:
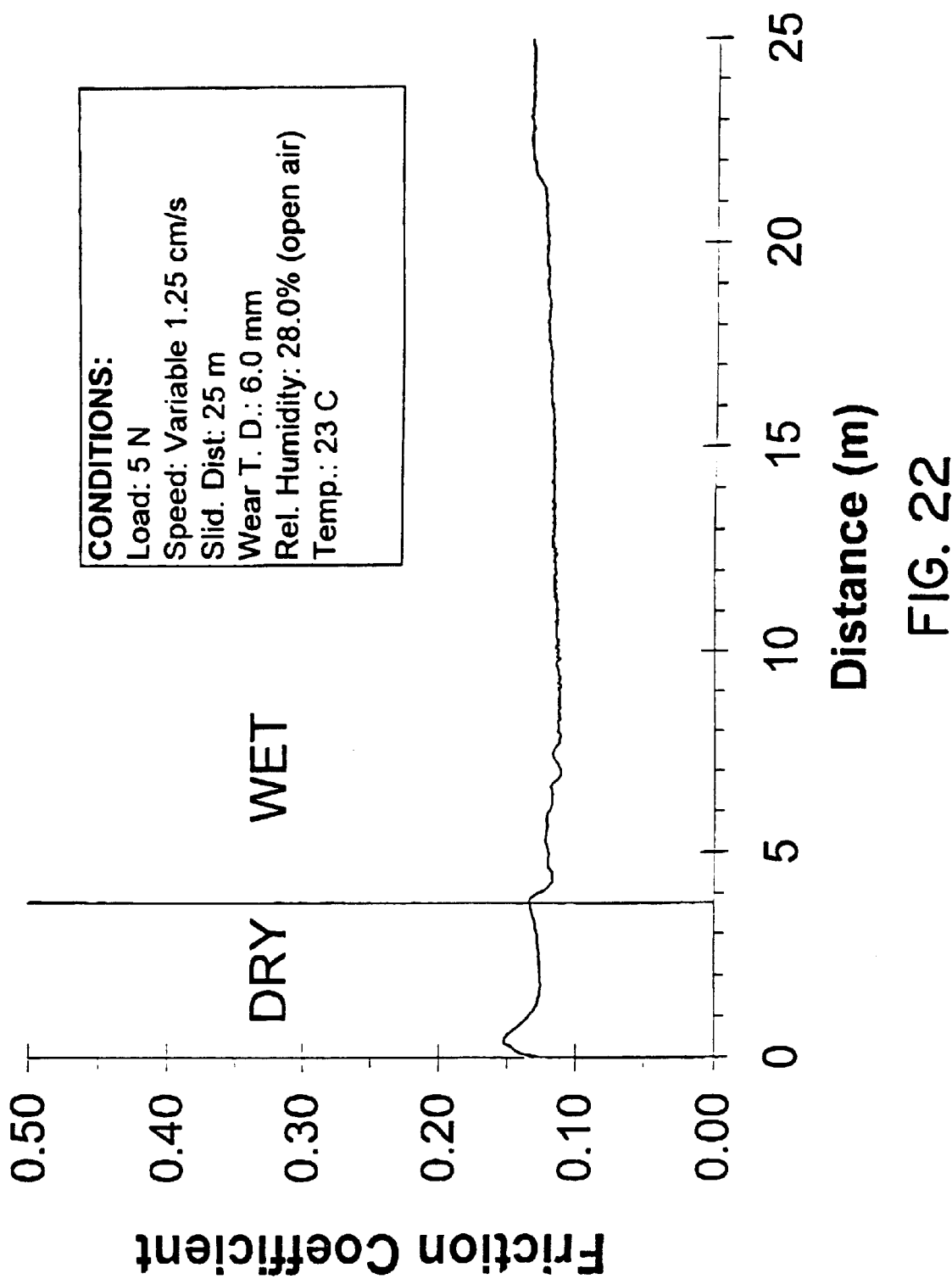

In some experiments, cracking of the furnace tube or leakage in sealing produced a noticeable oxygen contamination in the gas mixture. SiC chlorination reactions are sensitive to oxygen because of the high stability of $SiO_2$ and the volatility of CO and $CO_2$. In these experiments, a thin, translucent film formed around the outside of the specimen and specimen holder, separated from the specimen by distances of millimeters to centimeters. An example of this film can be seen in FIG. 18a. FIG. 18b shows the EDS spectrum from the film, showing that it contains only silicon and oxygen in the appropriate ratio for $SiO_2$. TEM and field emission SEM (inset in FIG. 18b) showed that the silica had a fibrous morphology similar to the products of active oxidation of silicon in low-pressure oxygen environment. This suggests that it formed via a reaction between $SiCl_4$ and oxygen contaminants in the gas environment. Thick carbon layers formed simultaneously with these active oxidation products, and there was no indication that this oxidation interfered with the growth of the carbon layer. This is in agreement with our thermodynamic calculation and shows that oxygen contamination does not produce a continuous silica that can act as a diffusion barrier and prevent the further film growth. This is important for scaling up the process, since oxygen is a common contaminant in chlorine gas and precise control over the environment in a large size industrial reactor may be difficult or expensive.

Analysis of Raman Spectra from Carbon Coatings

When the Raman data is simply taken in its raw state, one can state that for the adherent films on all types of SiC treated under all conditions the average positions of the D and G bands are 1345 $cm^{-1}$ and 1590 $cm^{-1}$, respectively with an $I_D/I_G$ ratio of about 0.95. The ratio of the intensities of these bands, $I_{D/G}$, has been shown to be proportional to $1/L_a$, where $L_a$ is the in-plane crystallite size of graphite in the range 2.5 nm<$L_a$<3000 nm:

$$L_a = 4.4(I_D/I_G)^{-1} \text{ (nm)}.$$

Using an $I_D/I_G$ ratio range of 0.80 to 1.20 for the treated samples one obtains an in-plane crystallite size of graphite in the range of 3.7<$L_a$<5.5 nm.

Properties

A brief summary of the properties is given in Table 2 in comparison with properties of various carbons and Hexoloy α-SiC measured using the same instruments.

TABLE 2

Properties Of The Developed Carbon Coatings In Comparison With SIC Ceramics And Carbons

| Material | Friction Coefficient (Air[1])/ Relative Wear Rate[2] | Friction Coefficient (Dry[1])/Relative Wear Rate[2] | Hardness (Gpa) | Young's Modulus (GPa) | Maximum Film Thickness |
|---|---|---|---|---|---|
| Graphite (HOPG) | 0.18/Low | >0.6/Very High | 1.1 | 9.7 | N/A (bulk) |
| Glassy Carbon | 0.14/Low | >0.6/Very High | 2.9 | 24 | N/A (bulk) |
| Hexoloy α-SiC | 0.5–0.7/Medium | 0.5–0.7/Medium | 50 | 550 | N/A (bulk) |
| $Cl_2$ Only Treated SiC(A) | 0.1/Very Low | 0.1/Very Low | 1.8 | 18 | Unlimited[4] |
| $Cl_2$ and $H_2$ Treated SIC(A) | 0.4–0.7/Medium | 0.4–0.7/Medium | ≦50 | ≦800 | Unlimited[4] |
| Diamond | 0.10–0.7/High to Low[3] | >0.7/Very High | 90–100 | 900–1000 | 1–10 μm |
| DLC | ≧0.05/High | ≧0.001/Very Low | 6–50[5] | 100–500[5] | 1–2 μm |

Notes:
[1]-Air is 8% relative humidity, Dry is 0.0% relative humidity dry $N_2$.
[2]-Wear Rate of material/coating and friction partner ($Si_3N_4$ ball).
[3]-Function of diamond film surface roughness.
[4]-The entire bulk piece of carbide can be converted to carbon.
[5]-Varies with hydrogen content and $sp^2/sp^3$ carbon bonding ratio.

Coatings produced by etching in $Cl_2$ have hardness and Young's modulus between that of graphite and glassy carbon. The same is true for primarily graphitic coatings obtained in gas mixtures with high chlorine to hydrogen ratios (2.98% $Cl_2$—0.74% $H_2$—Ar). However, coatings produced with a chlorine to hydrogen ratio of 2:1 has a hardness of ~40–50 GPa and a Young's modulus of ~600–800 GPa, which exceeds those of the SiC substrate and is similar to that of nanocrystalline diamond. They also exceed-the stiffness of DLC and are second only to single crystal diamond. By varying the process conditions and hydrogen to chlorine ratio, coatings with intermediate hardness and Young's modulus values were obtained.

PROSTHESES

Figure 31:
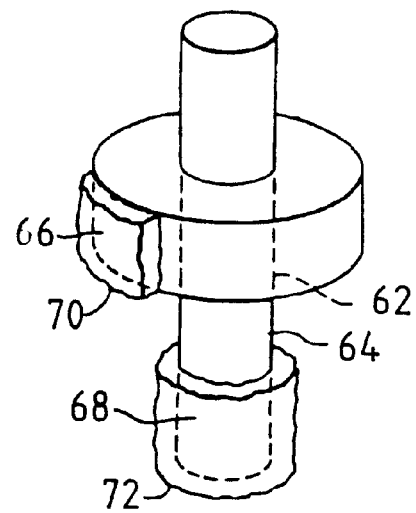
FIG. 31 schematically illustrates a pivot joint prosthesis adapted for forearm arthroplasty in accordance with the present invention.
Figure 32:
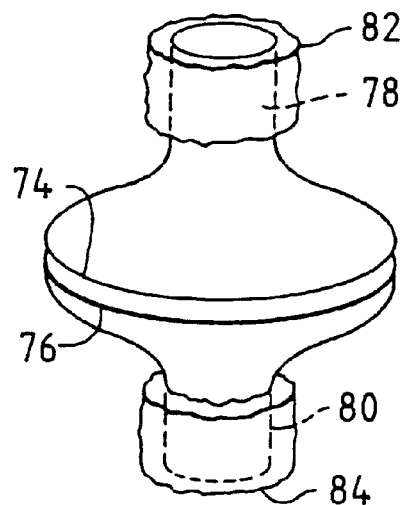
FIG. 32 schematically illustrates a gliding joint prosthesis adapted for carpus arthroplasty in accordance with the present invention.
Figure 33:
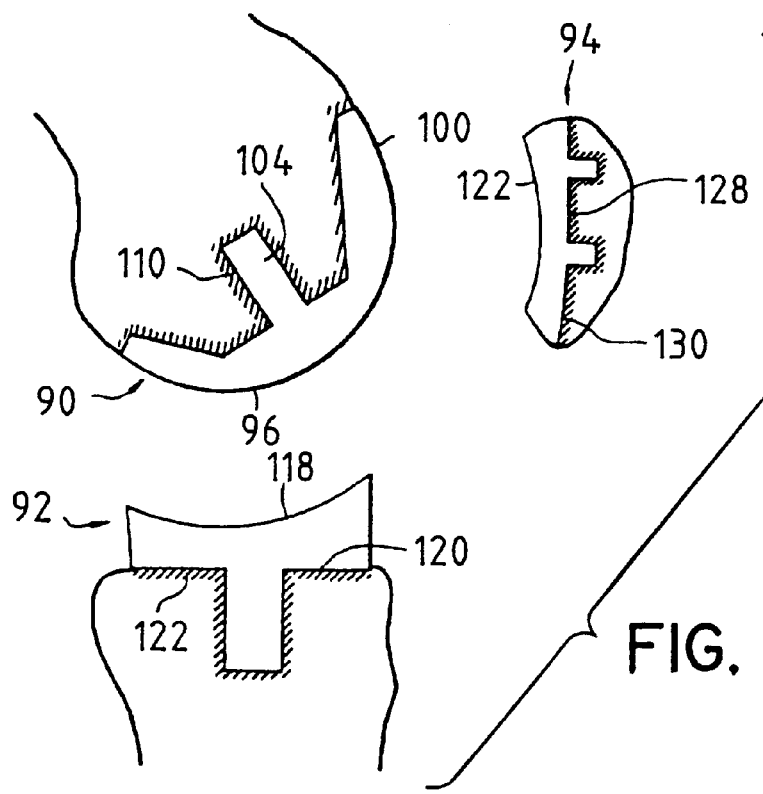
FIG. 33 schematically illustrates a complete knee joint prosthesis adapted in accordance with the present invention.

In accordance with one important embodiment of the present invention, as best shown in FIGS. 27–33, the carbon-surfaced material of the present invention is an excellent material for a prosthesis, surgically inserted via artheoplasty to restore or improve motion between bones of a skeletal joint, particularly a ball and socket shoulder joint (FIG. 27); a hinge joint prosthesis adapted for finger, elbow, and knee replacements (FIG. 28); an ovoidal joint prosthesis adapted for wrist arthroplasty (FIG. 29); a saddle joint prosthesis adapted for thumb joint arthroplasty (FIG. 30); a pivot joint prosthesis adapted for forearm arthroplasty (FIG. 31); a gliding joint prosthesis adapted for carpus arthroplasty (FIG. 32); and a complete knee joint prosthesis (FIG. 33).

One of the problems inherent in an extant prosthesis is that with continued wear, polymer (e.g., ultra high molecular weight polyethylene) or metal alloy debris accumulates in the joint. The contacting surfaces of the prosthesis made in accordance with the present invention should have an unlimited life without wear, while producing essentially no debris in the joint area. The joints, as shown in FIGS. 27–33 are preferably formed from monolithic metal carbide pieces with their respective shapes prior to etching with a halogen-containing gas at their respective articulating and anchor surfaces. Alternatively, the articulating and anchor surfaces can be machined after etching, provided that the etching process is carried out for a sufficient time such that the final articulating and anchor surfaces, after machining or otherwise shaping, are essentially only carbon on their mating surfaces.

Figure 27:
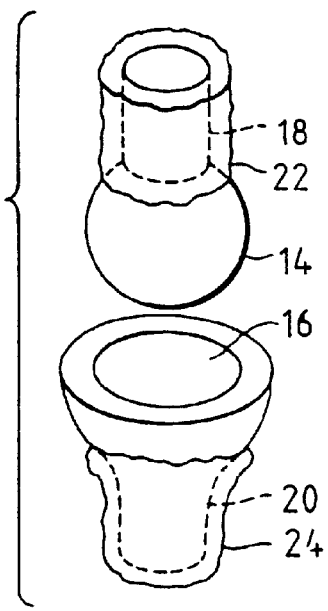
FIG. 27 schematically illustrates a ball and socket prosthesis adapted for shoulder arthroplasty in accordance with the present invention.
Figure 28:
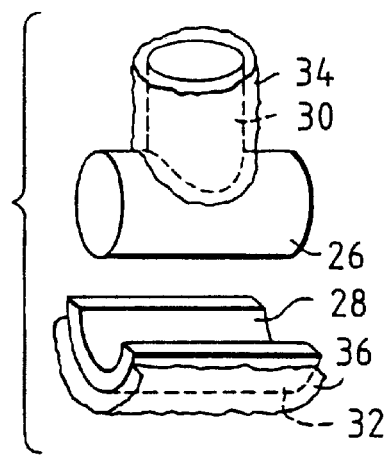
FIG. 28 schematically illustrates a hinge joint prosthesis adapted for finger, elbow and knee arthroplasty in accordance with the present invention.
Figure 29:
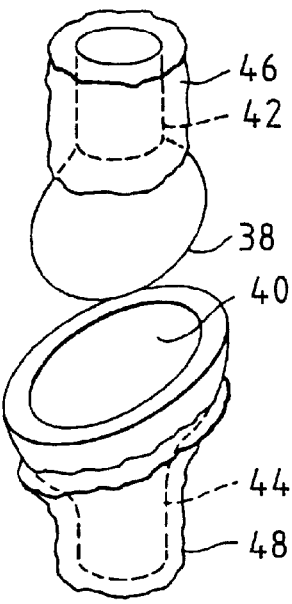
FIG. 29 schematically illustrates an ovoidal joint prosthesis adapted for wrist arthroplasty in accordance with the present invention.
Figure 30:
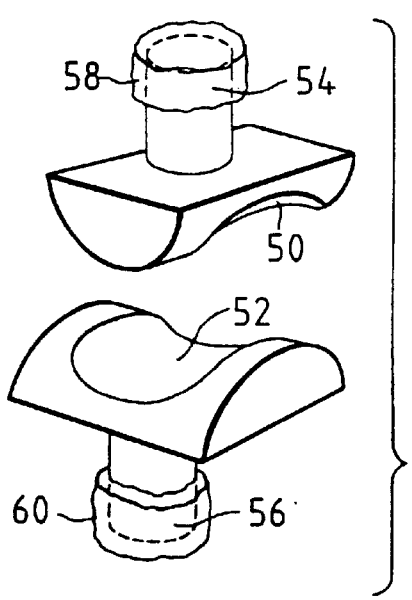
FIG. 30 schematically illustrates a saddle joint prosthesis adapted for thumb joint arthroplasty in accordance with the present invention.

FIG. 27 illustrates a hip or shoulder joint 12 comprising ball and socket articulating surfaces 14, 16, anchor surfaces 18, 20, and cement mantles 22, 24, allowing angular movement in any direction. FIG. 28 illustrates a joint for fingers, elbows, and knees, comprising hinged articulating surfaces 26, 28, anchor surfaces 30, 32, and cement mantles 34, 36, allowing angular movement only in one plane. FIG. 29 illustrates a joint for wrists, comprising ovoid articulating surfaces 38, 40, anchor surfaces 42, 44, and cement mantles 46, 48, the articulating surfaces being ovoidal so that only angular movement, but not rotation, of one bone in relation to the other is possible. FIG. 30 illustrates a thumb joint comprising articulating saddle surfaces 50, 52, anchor surfaces 54, 56, and cement mantles 58, 60, allowing movement in two orthogonal directions. FIG. 31 illustrates a forearm joint, comprising pivotal articulating surfaces 62, 64, anchor surfaces 66, 68, and cement mantles 70, 72, such that one bone pivots about its own longitudinal axis. FIG. 32 illustrates a carpal joint, comprising articulating glide surfaces 74, 76, anchor surfaces 78, 80, and cement mantles 82, 84, characterized by two flat surfaces that allow sliding in any planar direction.

FIG. 33 illustrates a more complicated joint configuration for knees that includes a femur-tibia joint and a femur-patella joint. This configuration includes a femoral member 90, a tibial member 92, and a patellar member 94. Preferably, the femoral member 90 has two articulating surfaces 96, 100 and one anchor surface 104 with cement mantle 110. Preferably, the tibial member 92 has one articulating surface 118 and one anchor surface 120 with cement mantle 121. Preferably, the patellar member 74 has one articulating surface 122 and one anchor surface 128 with cement mantle 130. The femur-tibia joint is a hinge joint similar to the hinge joint described with reference to FIG. 3 and comprises articulating surfaces 96, 118. The femur-patella joint is a sliding joint comprising articulating surfaces 100, 122, wherein the patellar member articulating surface 122 slides vertically within the femoral member articulating surface 100. In an alternative embodiment, the two femoral articulating surfaces 96, 118 are not discrete, but are contiguous.

In accordance with the present invention, the prosthesis of FIGS. 27–33 are halogen gas-etched at the articulating and anchor surfaces before or after molding to their desired dimensions, or throughout the prosthesis, to provide unexpectedly long wearing and low friction surfaces that do not create debris over the lifetime of the user. Theoretically, the prosthesis should be capable of effective use for the lifetime of the recipient and should never require repair or replacement.

BEARINGS, SEALS, VALVES

In accordance with an important embodiment of the present invention, mechanical parts made from halogen-etched metal carbides, form excellent bearing surfaces, valves and/or fluid seals when the sealing surface is converted to essentially only carbon. Such seals are useful in devices such as automotive water pumps, oil pumps, steam pumps, steam-powered valves, heart valves, pumps, torque converters, and in any environment where a fluid seal is required to prevent a gas or liquid from traveling from a higher pressure area to a lower pressure area such as a heart valve; and particularly where the seal is disposed adjacent to and infrictional contact with a moving part, such as a rotating shaft or a rotating seal adjacent to the moving part.

Figure 34:
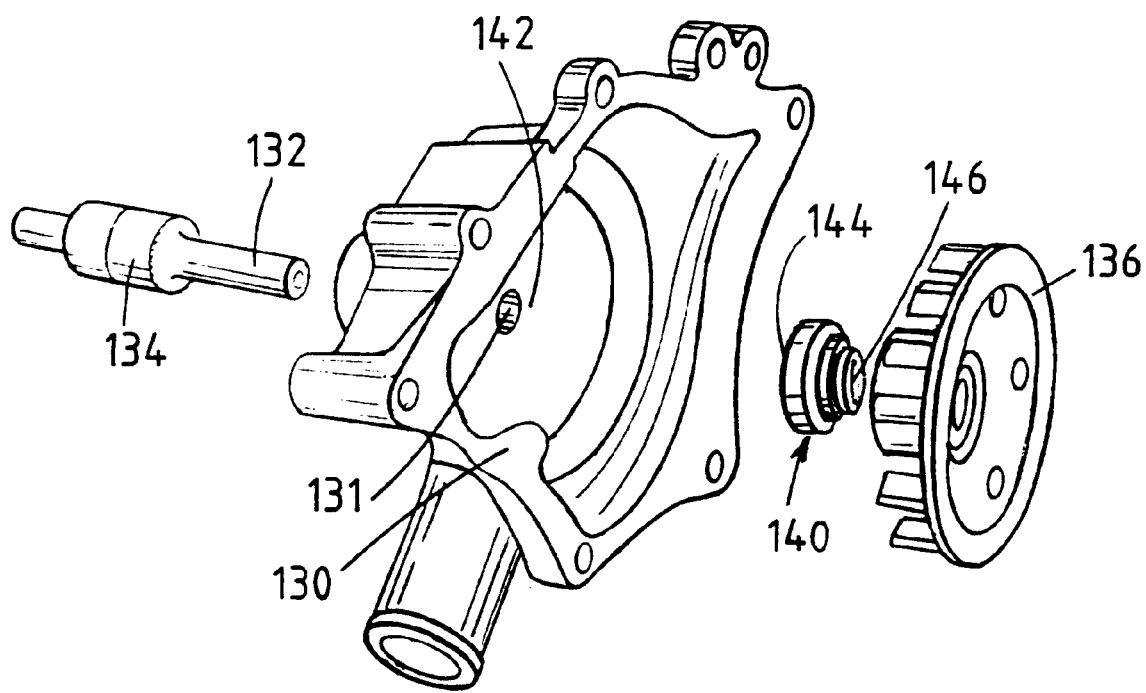
FIG. 34 is an exploded view of an automotive water pump showing a seal treated in accordance with the present invention.

As shown in FIG. 34, an automotive water pump generally includes a housing 130 (half of housing shown) having an aperture 131 for receiving pump shaft 132, carrying bearing 134. The shaft 132 is interconnected to an impeller 136 disposed within the housing 130. In order to prevent water from leaking out of housing 130 through the shaft-receiving aperture 131, along an outer periphery of the shaft 132, an annular sealing member 140 is disposed to surround the shaft 132 inside the housing 130 and in frictional contact with an inner surface 142 of the housing 130. The sealing member 140 may be press fitted or otherwise secured in position to the shaft, to spin with the shaft 132, at the inner surface 142 of the housing 130, causing continuous wear at the annular housing-contacting surface 144. Alternatively, the sealing member 140 may be spring biased against and secured in stationary position against the inner surface 142 of housing 130 such that the shaft 132 spins against an inner surface 146, of the sealing member 140 causing wear and eventual water leaking between the shaft and the inner surface 142 of the sealing member 140. This same principle applies to oil pumps, steam pumps, and the like. The sealing member 140 when halogen etched on its wear surface 144 or 146, prevents leakage indefinitely, or at least for the useful life of the automobile.

ELECTRICAL CONTACTS AND MICROSTRUCTURES

The halogen-etched materials of the present invention are excellent electrical conductors, wherein the resulting carbon surface is used as an electrical contact surface. Generally speaking, electrical conductors that are fabricated using the halogen etching process described herein may be used as electrical contacts within a variety of electromechanical devices such as circuit breakers, motors, contactors, relays, potentiometers (e.g., a wiper), rotary switches, slide switches, snap-acting switches, thermal switches, and the like. In particular, the carbon contact surfaces formed in accordance with the present invention are especially advantageous in electrical contact applications involving cyclical switching action and/or sliding or rotary contacts that are typically prone to excessive contact wear.

Electrical contacts made in accordance with the present invention may be formed from a silicon carbide or any other metal carbide starting material. For example, monolithic pieces of a metal carbide, which may be of any conventional geometry (i.e., cylindrical, rectangular, and the like), when halogen etched over the entire, or a portion of the, outer surface, make excellent brushes for electric motors. Of course, those skilled in the art will recognize that while a variety of metal carbide starting materials may be selected for use in forming an electrical contact, a particular starting material is typically selected to meet the environmental conditions and desired performance characteristics of a given application. For example, the desired cycle life, corrosion resistance, operating temperature range, maximum and minimum conduction current and voltage, as well as many other environmental conditions associated with the given application, may be used in determining the appropriate starting material.

The techniques described herein may also be used to create halogen-etched carbon surfaces on silicon-based microstructures such as integrated circuits and microelectromechanical systems (MEMS), which are well known in the art. Halogen-etched carbon surfaces may be created on these silicon-based microstructures to provide electrical contacts and/or to provide self-lubricating surfaces between moving components, which may, for example, include electrical contacts that slide, rotate, etc., on or within these microstructures.

For some applications, microstructures may be formed on a monolithic piece of silicon carbide using conventional etching techniques and the techniques of the present invention may be used to form halogen-etched carbon surfaces on selected portions of the microstructure. In other applications, the microstructure may include both silicon portions, which do not have any carbon surfaces, and silicon carbide portions, which may be halogen-etched in accordance with the present invention to form carbon surfaces thereon. In any event, those skilled in the art will recognize that the techniques of the present invention may advantageously used to form carbon surfaces for use in electrical contacts and/or self-lubricating surfaces on integrated circuits and complex electromechanical microstructures. By way of example only, the halogen-etched carbon surfaces of the present invention may be formed on the silicon carbide portions of a variety of well known silicon-based microstructures such as integrated circuits, pressure sensor diaphragms, accelerometers, switches, valves, fluid pumps, electric motors, and the like.

CATALYSTS, CATALYST SUPPORTS ION-EXCHANGE MATERIALS AND MOLECULAR SIEVES

As described, the halogen etched metal carbides have surprisingly high surface areas, where carbonized, and are useful as catalysts, catalyst supports, ion-exchange materials, and molecular sieves. The removal of the metal from the metal carbide starting material provides a microporous framework structures that provide carbon catalysts, and catalyst supports or co-catalysts for metallic catalysts such as Pd, Pt, Ru, Rh, Mn, Mg, Ni, Cr, Fe, Cu, and oxides, halides and oxyhalides of the foregoing metals. The formed carbon support can be activated, e.g., by washing with a strong acid and calcining at 350–550° C. to form a co-catalyst, and can accommodate a high percentage of metal catalyst because of the unusually high surface area of the formed carbon due to elimination of the metal from the metal carbide. Such catalysts can be used in catalytic cracking, hydrocracking; isomerization of parafins and substituted aromatics, e.g., xylene; disproportionation and alkylation of aromatics, such as toluene; dewaxing of distillate fuels and lube basestocks; and in converting lower ($C_1$–$C_3$) alcohols to hydrocarbons, e.g., gasoline.

The formed carbon includes pores having pore diameters in the range of 0.5 nm to 20 nm, generally about 0.5 nm to less than 2 nm, depending on the particular metal carbide that is halogen etched, so that the formed carbon is an excellent molecular sieve material that can function similarly to zeolites. The pores of the formed carbon adsorb gases, e.g., $H_2$, liquids, salts, elements, metal complexes, and the like, making the material excellent for ion-exchange, catalysis, and separation of materials by acting as a molecular sieve by intracrystalline diffusion in catalytic and adsorption applications, such as hydrogen storage. Templating or masking of the surface of the metal carbide before halogen etching can provide a desired pattern or path of pores.

As an ion-exchange material, the formed carbon can be treated with a liquid or gas to replace the halogen-removed metal from the metal carbide with a desired ion that is capable of ion-exchanging with ions of another material to form a product that contains the ions from the ion-supplemented carbon material. Suitable ions that can be exchangeably planted into the formed carbon material for ion-exchange include Ca, Na, Mg, Al, P, Na, K, Rb, Cs and the like. Because of the nature of the process of the present invention via metal removal, the formed carbon materials are unexpectedly efficacious in easy seeding of exchangeable ions to make unexpectedly efficient ion-exchange materials, e.g., in removal of antmonium ions, e.g., for waste water treatment; catalysts; catalyst supports and co-catalysts; and molecular sieves, e.g., in the separation and purification of radioisotopes, e.g., cesium and strontium radioisotopes for use in nuclear processing plants.

UNEXPECTED RESULTS (1) The highly disordered carbon layer formed on commercially available SiC by chlorination reactions at elevated temperatures has a friction coefficient up to seven times lower than the untreated SiC. The layer is adherent and actually shows a reduction in friction coefficient with time.

(2) The carbon layer with an optimal structure is relatively insensitive to loading and speed changes, maintaining a friction coefficient of about 0.10–0.12.

(3) The carbon layer shows little change in its friction coefficient when run polished or unpolished, wet or dry.

(4) As evidenced by the wear track features, the primary deformation process appears to be plastic flow of the carbon layer, resulting in a smooth, self-adjusting carbon layer as the wear process progresses.

(5) As the Raman $I_D/I_G$ peak ratio increased from 0.2 (micro-crystalline graphite) to around 1.0 (disordered carbon) the friction coefficient and wear rate of the coating layer also increased.

(6) Environmental Insensitivity: With further testing it has become clear that the carbon layer that we have made has unique tribological properties not found in any other carbon material. Specifically, when tested over a broad range of moisture content, the carbon material provides the same very low friction and wear rates (see attached figures and table). When HOPG Graphite, Glassy Carbon, and Diamond are tested in dry nitrogen at 0.0% RH their wear rates and friction coefficients are very high after a short time due to adhesion. Our carbon layer exhibits no such phenomenon and maintains its low wear rate and friction coefficient. Likewise, when diamond-like carbon is tested in air or with a small amount of oxygen present, its wear rate is greatly increased. Our carbon shows its same low wear rate and friction coefficient from low to high moisture and even submersed under water. This is a major claim, because the carbon can be used in a variety of environmental conditions with a predictable and efficient tribological response.

(7) The carbon layer has shown no dependence or relative speed of motion or increase in total load (see FIGS. 5a and 5b). In fact, the layer has passed a 4,000 rpm 32 psi dry wear test (as a coated mechanical seal) with little or no heating, no spallation, and virtually no wear. This is unprecedented for a carbon coating. In fact, diamond, diamond-like carbon, and various other coatings all failed the same test, performed by the manufacturer, due to spallation, chipping, or overheating of the seal which resulted in melting of the rubber retaining boot.

Figure 23:
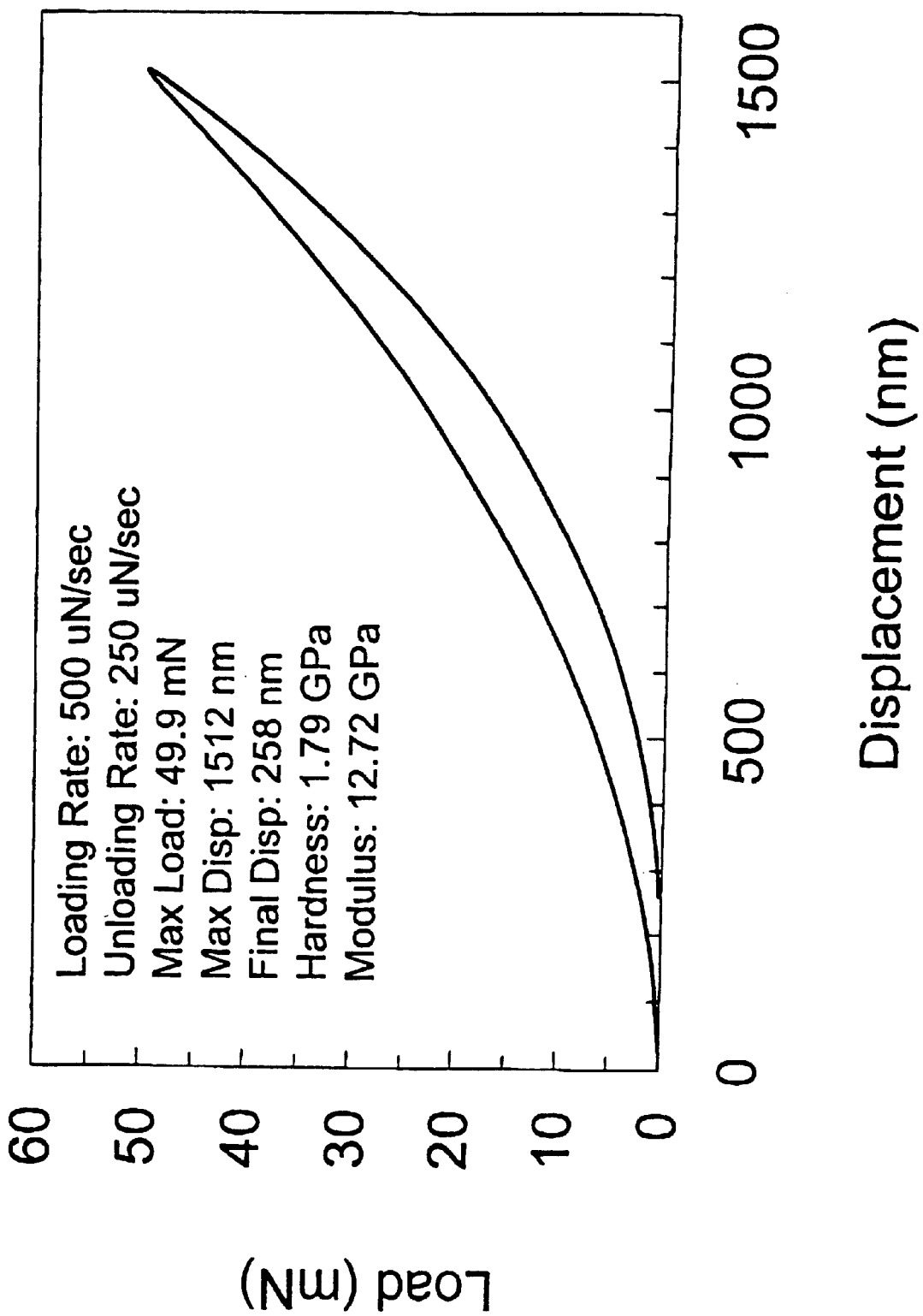
FIG. 23 is a graph showing the unusually high elastic response of the carbon coated materials of the present invention that is not present in other carbons of equivalent hardness and modulus.

(8) The carbon layer has shown a very elastic response (see FIG. 23) to loading not seen in other carbons of its equivalent hardness and modulus. It is theorized that the unusually high porosity of the formed carbon layer accounts, at least in part, for the unexpected elasticity. This is one of the reasons that the wear rates are so low even under severe loading and speed conditions.

Figure 24:
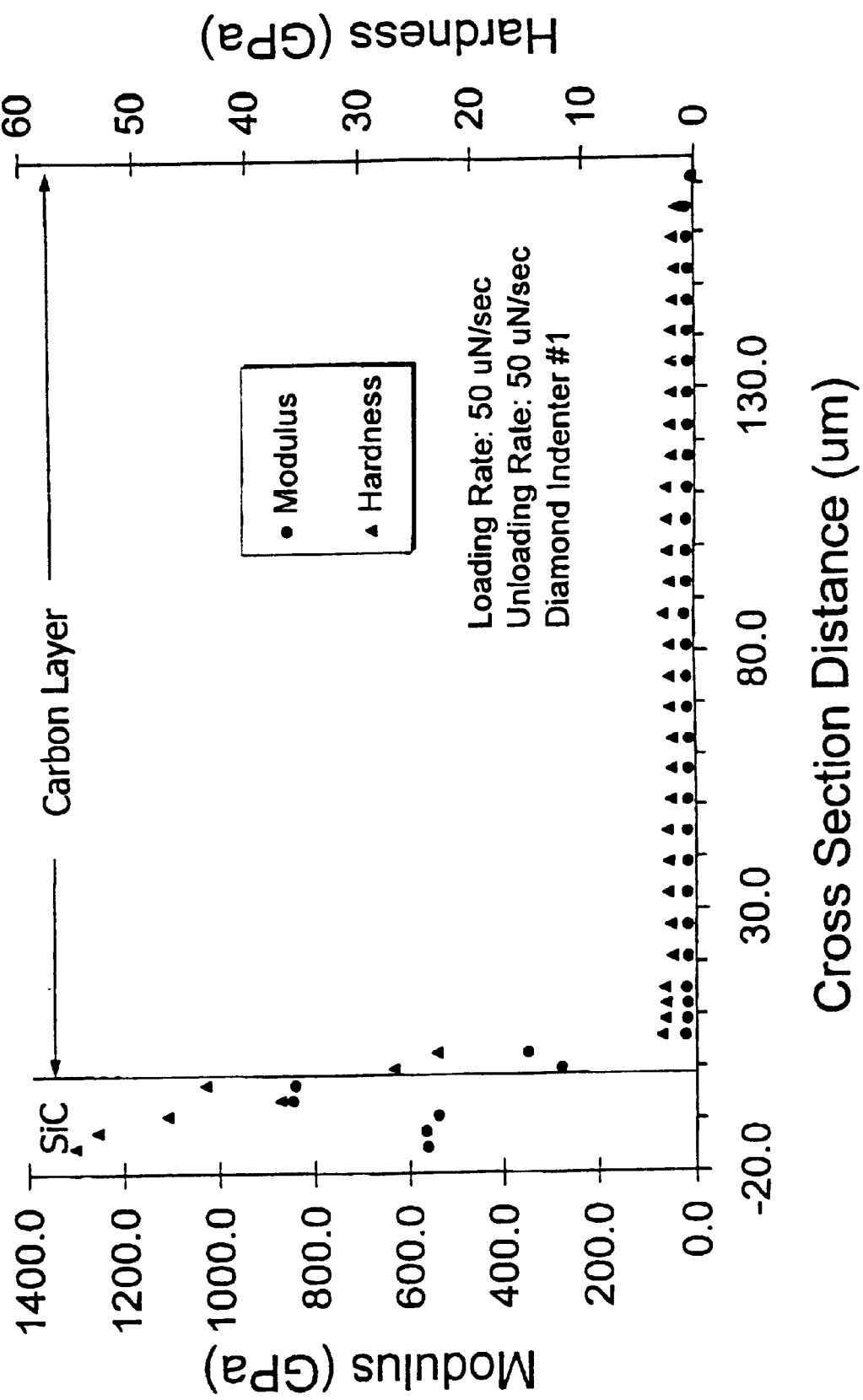
FIGS. 24 and 25 are graphs of modulus and hardness of SiC treated with 3.5% $Cl_2$, when indented with a load of 5 mN.
Figure 25:
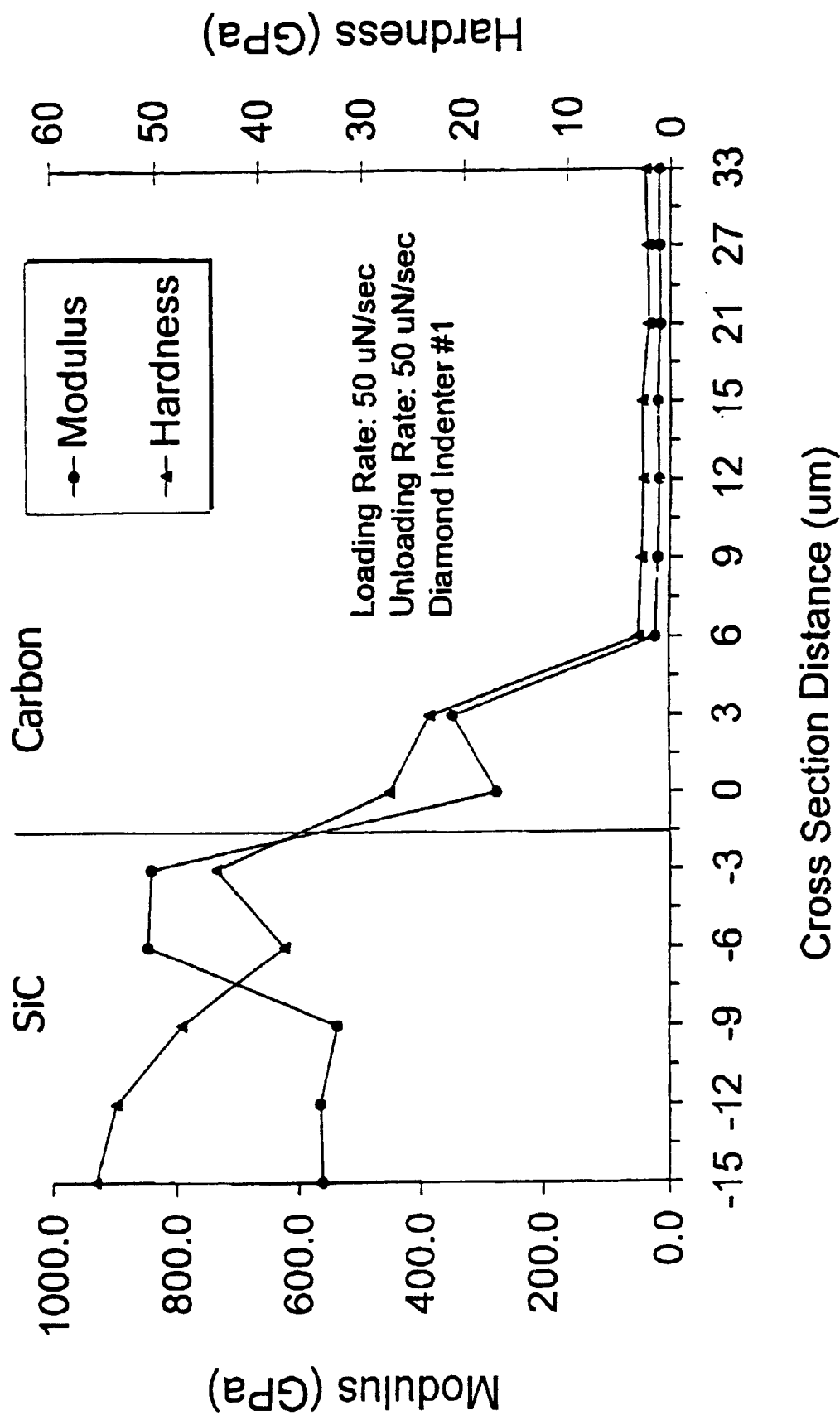
Figure 26:
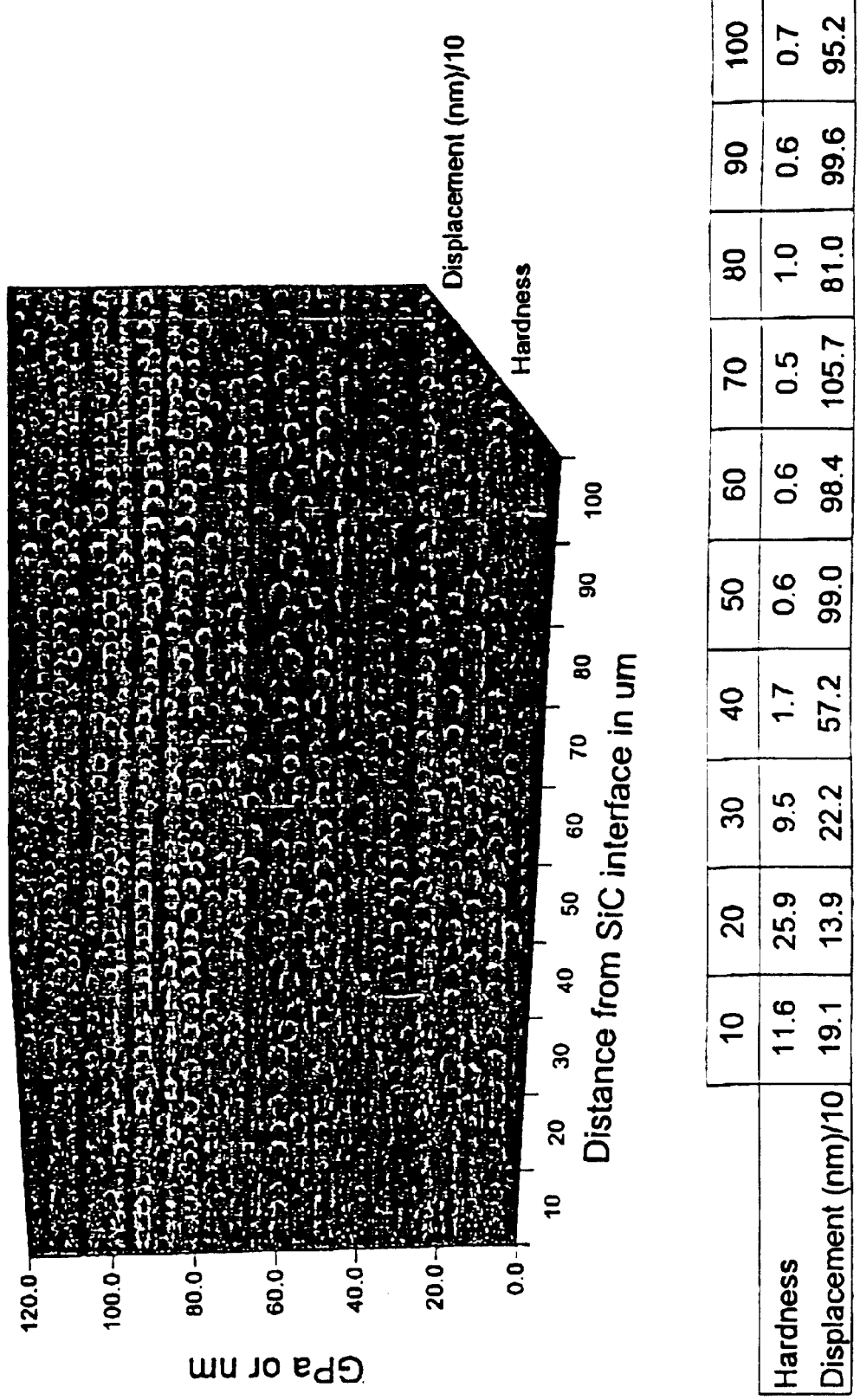
FIG. 26 is a graph showing maximum displacement and hardness of carbon coating produced in accordance with the present invention when SiC is treated with 3.5% $Cl_2$ (in Argon) for 24 hours at 1,000° C.

(9) After careful mechanical testing of the carbon/metal carbide interface, it was found that the interface region has a gradual transition in mechanical properties from the carbon layer to the metal carbide substrate (see FIGS. 24 and 25). This is important to ensure that the carbon layer will not spall, chip, or delaminate from the metal carbide substrate. In addition, this explains why the adhesion of our carbon layer is far superior to processes that deposit a material on the surface, vice convert it, and generate an interface with a large mismatch of properties instead of the gradual; gradation of properties.

(10) It has been shown, with nano-testing, that we can also vary the modulus and hardness of the carbon layer over a large range by simple, controlled additions of hydrogen gas to the reaction chamber. This is important because with a simple change in reaction gas we can tailor the final hardness, friction coefficient, wear rate, and modulus of the carbon coating to the application's requirements.

(11) When treated in $Cl_2$ with no hydrogen added, these coatings have physical and mechanical properties intermediate between graphite and glassy carbon. They demonstrate a low hardness (1.8 GPa), Young's modulus (18 GPa), very low wear rate and a friction coefficient of ~0.1, which is almost independent on the testing conditions (load, speed, and time) in dry or humid air. The coatings have been optimized for tribological properties, including use in dynamic seals, but may have many other applications as well.

(12) The analysis of Raman spectra from coatings produced in $Cl_2$—$H_2$ environments supports mixed $sp^2$–$sp^3$ bonding, or an impurity-carbon amorphous network. Further support to presence of $sp^3$ bonding is provided by a very high hardness (up to 50 GPa) and Young's modulus (up to 800 GPa) of these coatings.

(13) The developed technique is versatile because it allows for coatings of any thickness with hardness from 1.8 to 50 GPa and Young's modulus in the range from 18 to 800 GPa. Since similar results have been obtained on several different ceramics, including cubic and hexagonal SiC, pure SiC and SiC with sintering additives, we believe that the reported method can be used for synthesis of carbon coatings on a wide variety of SiC materials.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. An improved bearing disposed as part of a mechanical device, said mechanical device including a solid part in frictional contact with said bearing such that there is relative movement between said solid part and said bearing when the mechanical device is being operated, wherein the bearing includes a bearing surface in relative movement with respect to said solid part, said bearing surface having enhanced wear and friction properties by contacting a metal carbide, at a portion of said metal carbide that forms said bearing surface with a halogen-containing gaseous etchant having a halogen-containing gas concentration sufficient to remove metal from the metal carbide surface, at a temperature, pressure and for a time sufficient to provide said bearing surface on said metal carbide, said bearing surface having a surface gradient of hardness and Young's modulus comprising an adherent, non-spalling, non-separable, disordered carbon layer having a Raman peak intensity ratio of $I_D/I_G$ of 0.80 to 1.20, cross bonded between crystallite plates on the metal carbide and having a graphitized upper bearing surface.

2. The bearing of claim 1, wherein the bearing surface is a ball bearing surface in the shape of a sphere.

3. The bearing of claim 1, wherein the bearing surface is pointed, forming an end of a needle bearing.

4. The bearing of claim 1, wherein the bearing surface is cylindrical, forming a roller bearing.

5. The bearing of claim 1, wherein the bearing surface forms the bearing surface of a thrust bearing.

6. The bearing of claim 1, wherein the bearing surface is annular and surrounds a rotating shaft to seal a volume between said rotating shaft and said bearing surface to prevent fluid from flowing between said bearing surface and said rotating shaft when said shaft rotates.

7. The bearing of claim 6, wherein the seal is disposed in contact with a shaft of a water pump.

8. The bearing of claim 6, wherein the seal is disposed in contact with the shaft of an oil pump.

* * * * *

UNITED STATES PATENT AND TRADEMARK OFFICE
CERTIFICATE OF CORRECTION

PATENT NO. : 6,579,833 B1
DATED : June 17, 2003
INVENTOR(S) : Michael J. McNallan et al.

It is certified that error appears in the above-identified patent and that said Letters Patent is hereby corrected as shown below:

Title page, Item [54] and Column 1, lines 1-3,
Please change "PROCESS FOR CONVERTING A METAL CARBIDE TO CARBON BY ETCHING IN HALOGENS" to -- A PROCESS FOR CONVERTING A METAL CARBIDE TO CARBON ON THE SURFACE OF THE METAL CARBIDE BY ETCHING IN HALOGENS --.

Title page,
Item [57], ABSTRACT,
Line 4, please change "(he" to -- the --.

Signed and Sealed this

Eleventh Day of November, 2003

JAMES E. ROGAN
*Director of the United States Patent and Trademark Office*